(12) United States Patent
Shmukler et al.

(10) Patent No.: US 10,456,295 B2
(45) Date of Patent: Oct. 29, 2019

(54) MEDICAL DEVICE, ASSEMBLY AND METHOD FOR CREATING A CHANNEL IN SOFT TISSUE

(71) Applicants: SANOCULIS LTD., Haifa (IL); TEL HASHOMER MEDICAL RESEARCH INFRASTRUCTURE AND SERVICES LTD., Ramat Gan (IL)

(72) Inventors: Vadim Shmukler, Rishon Le'Zion (IL); Yoseph Glovinsky, Petah Tiqwa (IL)

(73) Assignees: TEL HASHOMER MEDICAL RESEARCH INFRASTRUCTURE AND SERVICES LTD., Tel Hashomer (IL); SANOCULIS LTD., Haifa (IL)

( * ) Notice: Subject to any disclaimer, the term of this patent is extended or adjusted under 35 U.S.C. 154(b) by 262 days.

(21) Appl. No.: 14/408,246

(22) PCT Filed: Jun. 13, 2013

(86) PCT No.: PCT/IL2013/050508
§ 371 (c)(1),
(2) Date: Dec. 15, 2014

(87) PCT Pub. No.: WO2013/186779
PCT Pub. Date: Dec. 19, 2013

(65) Prior Publication Data
US 2015/0127037 A1 May 7, 2015

Related U.S. Application Data

(60) Provisional application No. 61/659,603, filed on Jun. 14, 2012.

(51) Int. Cl.
*A61F 9/007* (2006.01)
*A61B 10/02* (2006.01)
(Continued)

(52) U.S. Cl.
CPC ...... *A61F 9/00781* (2013.01); *A61B 10/0275* (2013.01); *A61B 10/0283* (2013.01);
(Continued)

(58) Field of Classification Search
CPC .............. A61B 10/025; A61B 10/0266; A61B 10/0275; A61B 10/0283;
(Continued)

(56) References Cited

U.S. PATENT DOCUMENTS 3,683,892 A 8/1972 Harris
3,732,858 A 5/1973 Banko
(Continued)

FOREIGN PATENT DOCUMENTS

CN 200984221 Y 12/2007
EP 1815799 A1 8/2007
(Continued)

*Primary Examiner* — Katherine M Shi
*Assistant Examiner* — Lindsey Bachman
(74) *Attorney, Agent, or Firm* — Browdy and Neimark, P.L.L.C.

(57) ABSTRACT

The present disclosure provides a device, an assembly comprising the device and a method making use of same, the device comprising an elongated member extending between a first end and a second end, and a segment proximal to the second end extending along a longitudinal axis X, said segment comprises at least one depression axially extending along at least a portion of said segment and an external surface having a circumference C; and one or more blades with a cutting edge peripheral to C and the one or more blades extending along at least part of said segment; the first end comprising an engagement element for engagement with a grip unit comprising a rotor to cause rotation of said device about said axis upon actuation of the rotor and the second end comprising a tissue piercing tip. The device, assembly and method are useful in creating a channel in a (Continued)

biological soft tissue, such as a drainage channel in the sclero-corneal junction area of the eye. This may be useful in reducing intra-ocular pressure.

21 Claims, 13 Drawing Sheets

(51) Int. Cl.
 *A61B 17/3207* (2006.01)
 *A61B 17/16* (2006.01)
 *A61B 17/00* (2006.01)
(52) U.S. Cl.
 CPC ........... *A61B 17/320708* (2013.01); *A61B 17/320783* (2013.01); *A61B 17/1659* (2013.01); *A61B 17/320758* (2013.01); *A61B 2017/0023* (2013.01); *A61B 2017/320791* (2013.01)
(58) Field of Classification Search
 CPC .... A61B 17/320708; A61B 17/320758; A61B 17/320783; A61B 17/00791; A61F 9/007; A61F 9/00745; A61F 9/00754; A61F 9/00763; A61F 9/00772; A61F 9/00781
 USPC ................................. 606/159, 180; 600/567
 See application file for complete search history.

(56) References Cited

U.S. PATENT DOCUMENTS

| | | |
|---|---|---|
| 4,445,509 A | 5/1984 | Auth |
| 4,887,613 A | 12/1989 | Farr et al. |
| 4,895,166 A | 1/1990 | Farr et al. |
| 5,474,532 A | 12/1995 | Steppe |
| 5,893,862 A | 4/1999 | Pratt et al. |
| 5,968,058 A | 10/1999 | Richter et al. |
| 6,083,177 A * | 7/2000 | Kobren ............... A61B 10/0275 600/564 |
| 6,361,504 B1 | 3/2002 | Shin |
| 7,344,546 B2 | 3/2008 | Wulfman et al. |
| 7,914,463 B2 * | 3/2011 | Tarter ................ A61B 10/0275 600/567 |
| 2002/0095101 A1 | 7/2002 | Fontenot |
| 2003/0004528 A1 * | 1/2003 | Ishikawa ............ A61B 17/3415 606/169 |
| 2004/0167428 A1 | 8/2004 | Quick et al. |
| 2005/0080441 A1 | 4/2005 | Dodge et al. |
| 2005/0203441 A1 | 9/2005 | Voegele |
| 2006/0052722 A1 * | 3/2006 | Brautigam ......... A61B 10/0266 600/567 |
| 2006/0241580 A1 * | 10/2006 | Mittelstein ......... A61B 18/1482 606/41 |
| 2009/0024057 A1 * | 1/2009 | Owen ................ A61B 1/00094 600/581 |
| 2009/0112119 A1 * | 4/2009 | Kim ................... A61B 10/0266 600/564 |
| 2009/0204021 A1 | 8/2009 | Shabaz et al. |
| 2009/0306657 A1 | 12/2009 | Piippo et al. |
| 2009/0306691 A1 | 12/2009 | Cambronne et al. |
| 2010/0262147 A1 | 10/2010 | Siegal et al. |
| 2011/0105944 A1 | 5/2011 | Ohnishi et al. |
| 2011/0144671 A1 | 6/2011 | Piippo Svendsen et al. |
| 2012/0245487 A1 * | 9/2012 | Eells ................... A61B 10/0275 600/567 |

FOREIGN PATENT DOCUMENTS

| | | |
|---|---|---|
| JP | H9504979 A | 5/1997 |
| JP | 10201764 A | 8/1998 |
| JP | 2003024339 A | 1/2003 |
| JP | 4705201 B2 | 6/2011 |
| RU | 2212848 C2 | 9/2003 |
| RU | 89380 U1 | 12/2009 |
| RU | 2385694 C1 | 4/2010 |
| SU | 567447 A1 | 8/1977 |
| SU | 1456115 A1 | 2/1989 |
| WO | 95/24858 A1 | 9/1995 |
| WO | 2004080345 A2 | 9/2004 |
| WO | 2010118172 A1 | 5/2010 |

\* cited by examiner

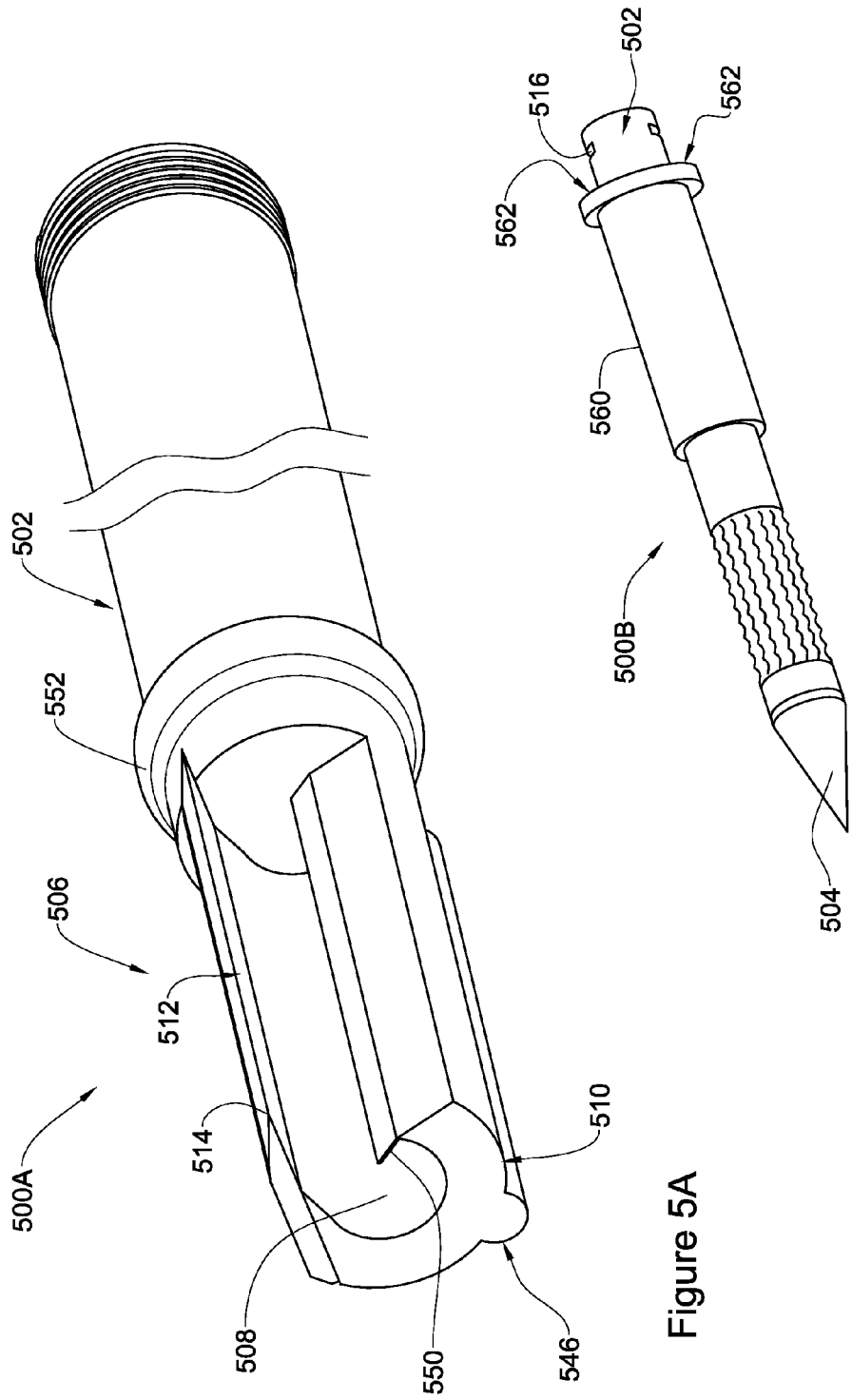

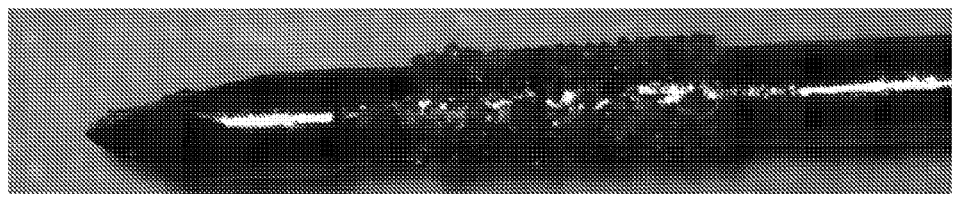
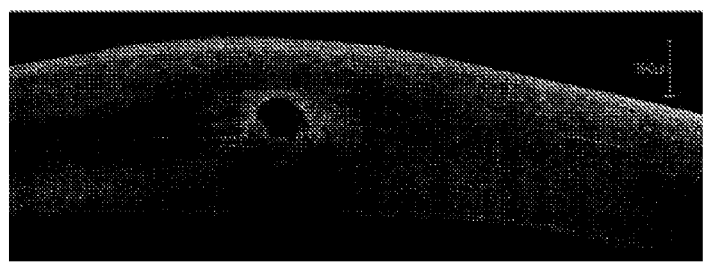
Fig. 13A
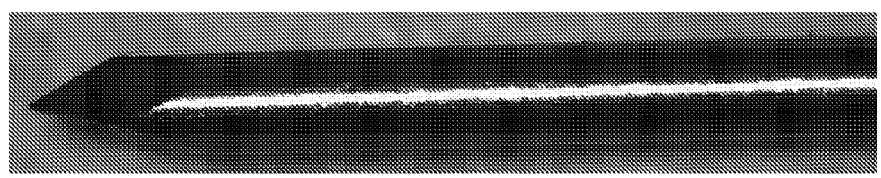
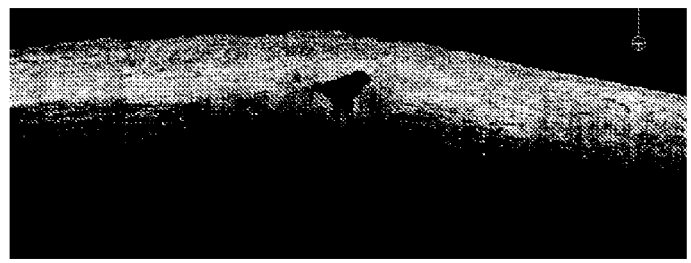
Fig. 13B

MEDICAL DEVICE, ASSEMBLY AND METHOD FOR CREATING A CHANNEL IN SOFT TISSUE

FIELD

The present disclosure relates to the field of medical devices.

BACKGROUND

In medicine, a need frequently arises to cut and remove small volumes of tissue from the body as a treatment or for diagnosis purposes. This may be essential for example during acquiring tissue for a biopsy, removing calcification from inner walls of obstructed blood vessels or creating paths for drainage of excessive liquids such as in Glaucoma condition.

Tools are available for cutting soft as well as hard tissues in the body. One example is presented in U.S. Pat. No. 6,361,504 which provides a hollow tubular shaped biopsy needle having a hollow elliptical cross section shaped lumen therethrough, and the method for fabricating the needle and the apparatus for operating the needle.

In addition, U.S. Pat. No. 7,344,546 describes a device for intralumenal removal of tissue from inside blood vessels using an advanceable and rotatable cutter assembly designed for differential cutting. One embodiment of the cutter assembly includes a cutter with blades that are designed and arranged to form an acute blade angle of attack with the matter-to-be-removed. The cutter assembly is axially advanceable by translating the drive shaft and rotatable by rotating the drive shaft. The occlusive material is scraped by the cutter assembly and may be aspirated to remove the material from the body cavity. The cutter assembly may provide aspiration ports positioned between facing surfaces of the blades.

Further, U.S. Pat. No. 4,887,613 discloses a cutter that penetrates at its forward end into, and excises, obstructive tissue in a lumen in a living being by providing two spaced external segments of a conical generally hollow portion with cutting surfaces at their edges. The cutter may have a forward portion of restricted dimensions to facilitate the penetration of the cutter into the obstructive tissue. A progressively expanding portion such as a truncated cone extends rearwardly from the portion of restricted dimensions. In this way, the cutter expands the area of excision of the obstructive tissue from the lumen wall at progressive positions rearwardly from the forward end. The obstructive tissue in the lumen at the progressively expanding positions may be excised at the positions of penetration of the obstructive tissue by rotating the cutter manually or by a motor. The cutter may also have a hollow portion of substantially constant dimensions, such as a hollow cylinder, at the laterally expanded end.

GENERAL DESCRIPTION OF THE PRESENT DISCLOSURE

The present disclosure provides, in accordance with a first of its aspects a device comprising an elongated member extending between a first end and a second end, and a segment proximal to the second end extending along a longitudinal axis X, said segment comprises at least one depression axially extending along at least a portion of said segment and an external surface having a circumference C; and one or more blades with a cutting edge peripheral to C and the one or more blades extending along at least part of said segment; the first end comprising an engagement element for engagement with a grip unit comprising a rotor to cause rotation of said device about said axis upon actuation of the rotor and the second end comprising a tissue piercing tip.

The present disclosure also provides a device comprising an elongated member extending between a first end and a second end and comprising a segment proximal to the second end extending along a longitudinal axis X, said segment comprises roughened external surface protruding outwardly from a circumference C; the first end comprising an engagement element for engagement with a grip unit comprising a rotor to cause rotation of said device about said axis upon actuation of the rotor, and the second end comprising a tissue piercing tip.

In accordance with a second aspect, the present disclosure provides a medical assembly comprising a grip unit comprising a shank with a rotating end and having mounted on the rotating end a device as defined herein; and a rotor operable to rotate said device around said axis X.

Yet, the present disclosure provides in accordance with a third aspect, a method for creating a channel in a biological soft tissue, the method comprises providing a medical assembly comprising a grip unit and a device mounted thereon, the device being as disclosed herein;

piercing the biological tissue with the tissue piercing tip of the device and sliding the device into the soft tissue to a desired depth within the soft tissue;

actuating said medical assembly while the device is embedded in the soft tissue to allow at least one full rotation about said axis X, during said rotation soft tissue is scrapped around the external surface of said segment; and upon termination of rotations, removing the device from the soft tissue, leaving a channel within said tissue.

The device, assembly and method disclosed herein are particularly suitable for creating a channel in the sclero-corneal junction of a subject's eye. In some embodiments, this may be used for reducing intraocular pressure. Thus, the present disclosure also provides a method for reducing intraocular pressure, the method comprises creating a drainage channel in the sclero-corneal junction area of the eye and communicating the anterior chamber of the eye with the interface between the sclera and the conjunctiva, the drainage channel having a diameter of no more than 200 µm, as determined after pulling the device out and allowing the sclera tissue to recoil.

BRIEF DESCRIPTION OF THE FIGURES

In order to understand the disclosure and to see how it may be carried out in practice, embodiments will now be described, by way of non-limiting example only, with reference to the accompanying figures, in which:

FIGS. 5A-5B are isometric views of devices in accordance with two alternative embodiments of the present disclosure;

FIG. 13A-13B are images of channels formed with a piercing tool without blades (FIG. 13A) or with a device according to the present disclosure (FIG. 13B);

DETAILED DESCRIPTION OF EMBODIMENTS

The present disclosure is directed to a device configured and operable to cut and remove soft tissue in a well-defined manner including, but not limited to, the shape and volume of the excised tissue, in relatively short duration, with minimum invasion and consequently minimum discomfort to the treated subject.

In accordance with a broadest aspect of the present disclosure, there is provided a device comprising an elongated member extending between a first end and a second end, and a segment proximal to the second end extending along a longitudinal axis X, said segment comprises at least one depression axially extending along at least a portion of said segment and an external surface having a circumference C; and one or more blades with a cutting edge peripheral to C and the one or more blades extending along at least part of said segment; the first end comprising an engagement element for engagement with a grip unit comprising a rotor to cause rotation of said device about said axis X upon actuation of the rotor and the second end comprising a tissue piercing tip. In this connection, reference is made to FIGS. 1A and 1B providing an illustration of a device 100 in accordance with one non-limiting embodiment of the present disclosure.

Figure 1A:
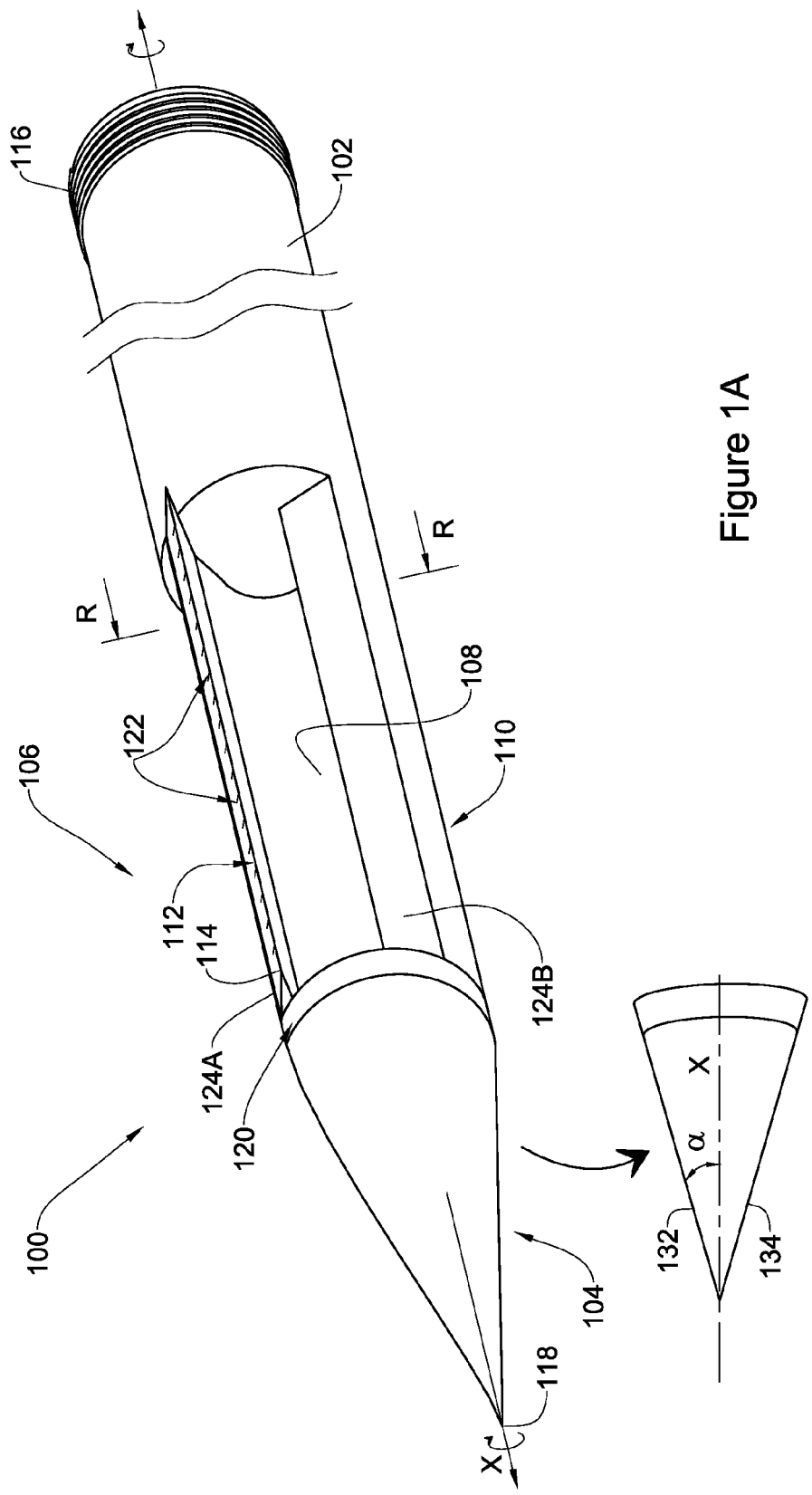
FIGS. 1A and 1B are an isometric view and a transverse cross sectional view of a device according to a non-limiting embodiment of the present disclosure.
Figure 1B:
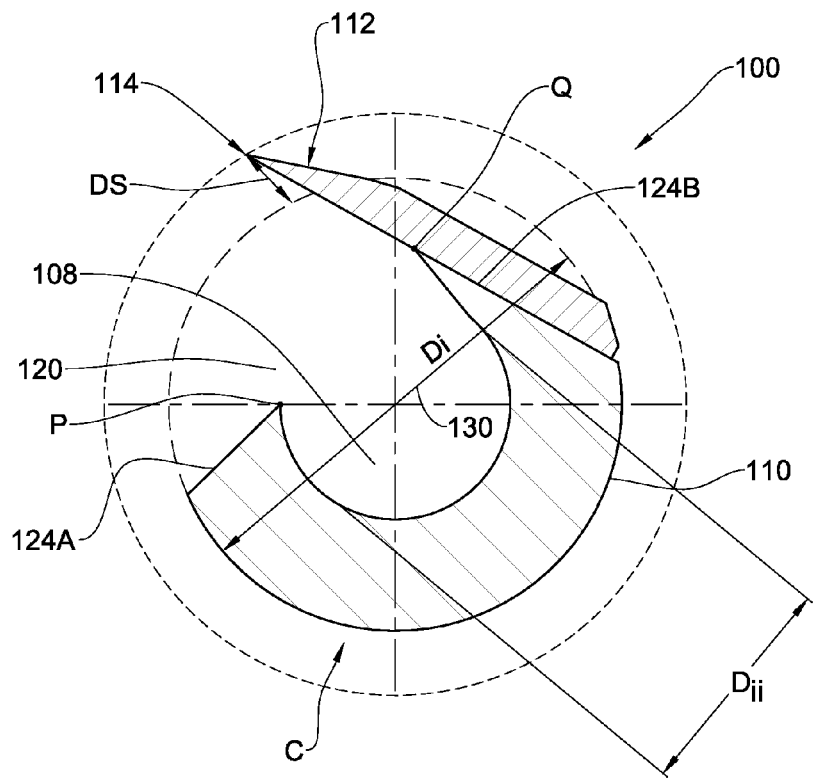

Specifically, FIG. 1A, discloses a device 100 comprising an elongated member extending between a first end 102 and a second end 104 constituting a tissue piercing tip, and a segment 106 extending from the second end 104 along a longitudinal axis X to the first end 102. The segment 106 comprises at least one depression 108 defined between two essentially parallel rims 124A and 124B and axially extends along at least a portion of the segment 106, and an external surface 110 having a circumference C as is also illustrated in FIG. 1B. In this specific embodiment of FIG. 1A, the second end 104 is sealed and the segment 106 includes a single depression 108 which extends from the sealed end 104 along the entire length of segment 106.

Further as illustrated in the embodiment of FIG. 1A, device 100 comprises a single blade 112 extending along segment 106 with a cutting edge 114 peripheral to C. As may be appreciated by a person versed in the art, similar to the illustration provided in FIG. 1A, the device may include more than one blade (e.g. plurality of blades). The two or more blades may be positioned in various forms. For instance, a series of discrete blades may be lined coaxially with axis X on one of rims 124A or 124B of depression 108. In some other embodiments, the more than one blade may be distributed either in a pattern or essentially randomly over external surface 110, each blade being constructed with a respective depression configured to collect tissue scraped from the surrounding upon rotation of the device. In some embodiments the plurality of blades and depressions may be constructed similar to grating slots in a kitchen grater (not illustrated).

While blade 112 is illustrated in FIG. 1A as a straight blade (i.e. cutting edge 114 having zero curvature), in some embodiments, the at least one blade 112 has a curved cutting edge (not shown). This can be useful in creating various shapes of void or channel in the area of the tissue being excised, as further discussed below.

The first end 102 of device 100 typically includes an engagement element 116, in this particular embodiment illustrated as an internal (male) thread to be paired with a fitting external (female) thread of a grip unit (not shown) comprising a rotor to cause rotation of the device about the axis X upon actuation of the rotor. The engagement element may be in the form of thread, screwing, interlock, shank or any other suitable mechanism for connecting to parts of a device.

Second end 104 which is illustrated in this particular embodiment of FIG. 1A is beveled, with a tissue piercing tip 118 being collinear with the axis X. When spotted from the side, the second end is beveled with a tip angle α being the angle between the axis X and each of the second end's beveled sides 132 and 134. The magnitude of the angle α may vary towards making the piercing of the tissue as comfortable as possible to the treated being. In some embodiments, beveled end is designed to have a tip angle of between 5° and 15°. The exact degree is a function of the length of the second end 104 along axis X and the dimensions circumference C of the device 100.

In some embodiments (not illustrated in this figure) the second end may be conical with the tissue piercing tip being collinear with axis X such that the cone point angle is between 10° and 30°.

The segment 106 is preferably sealed at the junction with second end 104. Thus, even if second end 104 has a tubular lumen (not shown), e.g. as in a medical needle, there would be no fluid communication between such lumen and depression 108. At times, segment 106 and second end 104 are gaped by a reinforcement gap section (a type of a collar) such as gap section 120 that is preferably sealed, i.e. devoid of any depression. In some embodiments, and typically depending on the particular application of the device, the gap section 120 has a length (along longitudinal axis X), defined between the interfaces with the second end 104 and with the segment 106 of between 200-2500 µm. This particular embodiment may be suitable for creating a channel in the wall of the eye, e.g. in the sclera and sclero-corenal junction, as further discussed below.

Further, device 100 may comprise scale markers 122 extending along at least a portion of the device. For example, along a portion from second end 104, (e.g. starting from piercing tip 118) or along a portion comprising second end 104 and at least a portion of segment 106. The scale markers 122 are typically used for identifying distances along longitudinal axis X. For example, scale markers 122 may be used to define depth of penetration of the device 100 into a soft tissue or, in other words, distance from second piercing tip 104. In some embodiments, the scale markers are distributed along the external surface 110.

External surface 110 has a circumference C with an essentially uniform circular cross-sectional shape being transverse to longitudinal axis X. As such, external surface 110 traces external contours of a cylinder.

An exemplary transverse cross section of segment 106 along line RR in FIG. 1A is illustrated in FIG. 1B. For simplicity, like reference numerals to those used in FIG. 1A, are used in FIG. 1B to identify components in FIG. 1B having a similar function. For example, component 108 in FIG. 1B is a depression having the same function as depression 108 in FIG. 1A.

In FIG. 1B, a cross section of segment 106 of device 100 is shown, comprising a circumference C having a circular external surface 110 with depression 108 extending between points P and Q; and a blade 112 extending from said external surface 110 with a cutting edge 114 peripheral to C and with a radial distance DS from circumference C. The external surface of segment 106 may be defined by a diameter Di along line 130. In some embodiments, diameter Di has a nominal value of between 100-1,000 µm, depending on the particular application of the device, e.g. at different parts or organs of the body and/or in different species. The device may also be defined by an internal diameter Dii of the depression. As appreciated, the dimensions of Dii will be dictated by the dimensions (diameter) of the channel to be created. Thus, for a channel having a diameter, for example, of 100 µm, the device to be used is one having a diameter Dii of about 100 µm.

Similarly, depending on the design and application of the device, depression 108 may vary in its length L along longitudinal axis X. In some embodiments, L may be between 100 to 2,500 µm, or even between 800-1,500 µm.

As will be further detailed below, in operation, tissue that surrounds external surface 110 of circumference C is cut by blade 112 upon rotation of the device around its axis X. Typically, a layer with a thickness equal or less than DS is cut and received in depression 108. While in this particular embodiment, blade 112 is connected to the device via point Q, the blade may similarly be connected via point P. In some embodiments, distance DS is between about 2 to 100 µm.

The dimensions of the depression and the number of rotations independently may define the volume of tissue to be received in the depression. The dimensions of the depression (its internal diameter Dii) may provide an upper limit to the amount of tissue to be received such that once the depression is full, no more tissue will be cut. In addition, the number of rotations dictates the number of thin tissue layers scraped off the surrounding, when each rotation provides within the depression an additional volume of tissue.

Figure 2A:
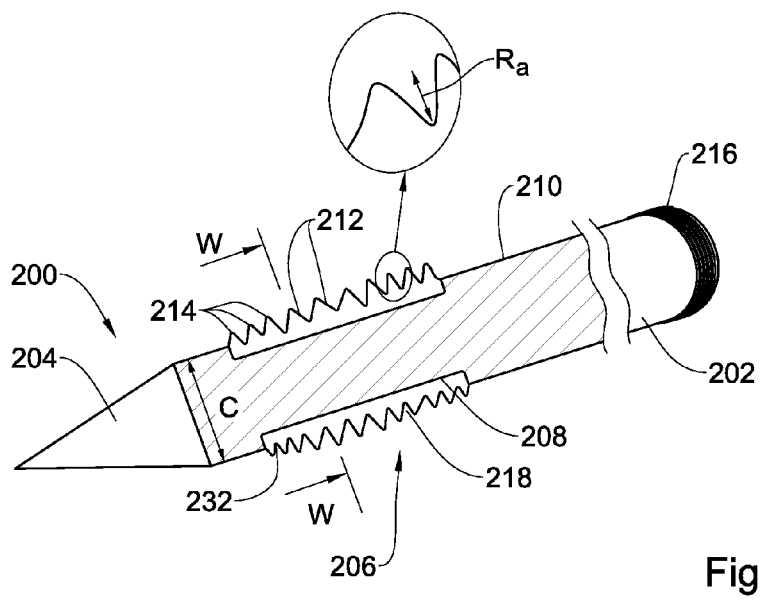
FIGS. 2A and 2B are an isometric view and a transverse cross-sectional view of a device in accordance with another embodiment of the present disclosure.
Figure 2B:
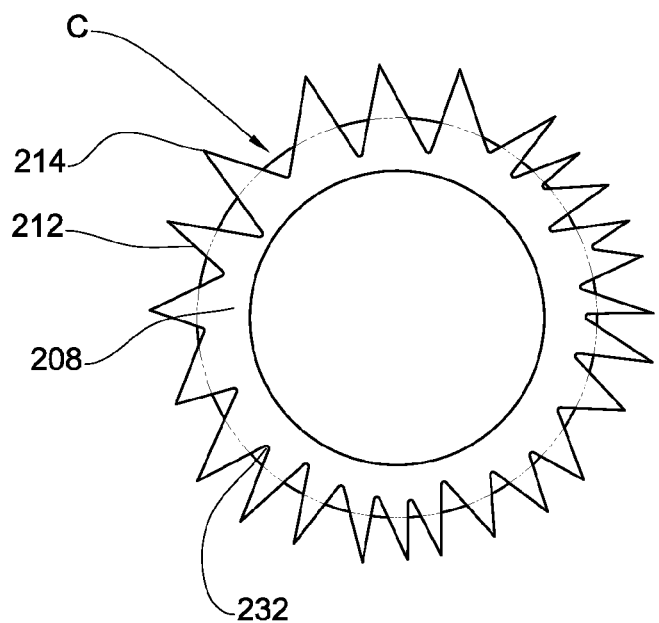

An alternative embodiment is disclosed in FIGS. 2A and 2B. For simplicity, like reference numerals to those used in FIGS. 1A-1B, shifted by 100 are used to identify components having a similar function in FIGS. 2A and 2B. For example, component 202 in FIG. 2A is a first end having the same function as first end 102 in FIG. 1A.

Specifically, device 200 comprises an elongated member extending between a first end 202 constituting an engagement element, and a second end 204 constituting a tissue piercing tip, and a segment 206 extending from the second end 204 along a longitudinal axis to the first end 202. The segment 206 has an external surface 210 with a circumference C and comprises a depression 208 extending longitudinally and circumferentially along at least a portion of the segment 206. At least part of segment 206 is coated with a plurality of blades 212, which in the present illustration appear as a plurality of protrusions with cutting edges 214 peripheral to circumference C (like a ridge and a valley). In some embodiments, the plurality of protrusions is in the form of a roughened surface functioning as a file-like surface and protruding outwardly from circumference C. In some embodiments, the roughened surface is provided by coating segment 206 with diamond dust (synthetic diamond cover of a cutting tool). The roughness of the surface may be defined as Ra, being an average height of the protrusions (similar to Ra used for defining a file tooth average height or "diamond dust" height).

When the device comprises a roughened surface it may be defined as one comprising an elongated member extending between a first end and a second end and comprising a segment proximal to the second end extending along a longitudinal axis X, said segment comprises roughened external surface protruding outwardly from circumference C; the first end comprising an engagement element for engagement with a grip unit comprising a rotor to cause rotation of said device about said axis upon actuation of the rotor and the second end comprising a tissue piercing tip. Characteristics of the various elements of this embodiment are as defined herein above and below with respect to devices in accordance with other embodiments of the present disclosure.

In operation, the device in accordance with the present disclosure is rotated and the plurality of protrusions scrap off tissue surrounding the coated segment in small pieces (i.e. debris). The rotation of device 200 may be terminated after a defined number of rotations, e.g. when the valleys between the protrusions are expected to be filled with tissue debris, and no more tissue can be scraped off which will result in the device rotating freely.

In some embodiments, the plurality of blades may not exceed circumference C. According to this embodiment, the device comprises an elongated member extending between a first end and a second end, and a segment proximal to the second end extending along a longitudinal axis X, said segment comprises at least one depression axially extending along at least a portion of said segment and an external surface having a circumference C; and one or more blades with a cutting edge extending up to circumference C and the one or more blades extending along at least part of said segment; the first end comprising an engagement element for engagement with a grip unit comprising a rotor to cause rotation of said device about said axis upon actuation of the rotor and the second end comprising a tissue piercing tip.

In some other embodiments, the plurality of blades coat at least a portion of the elongated member extending between the device's first end and second end, preferably at the segment proximal to the second end, albeit without having a dedicated depression for carrying the blades. According to this embodiment, the device comprises an elongated member extending between a first end and a second end, and a segment proximal to the second end extending along a longitudinal axis X, said segment comprises an external surface and one or more blades with a cutting edge extending on external surface along at least part of said segment; the first end comprising an engagement element for engagement with a grip unit comprising a rotor to cause rotation of said device about said axis upon actuation of the rotor and the second end comprising a tissue piercing tip, the piercing tip having a triangular cross section.

The dimensions of a device in accordance with the present disclosure, such as device 100 or device 200 depend on its application. In some embodiments, a device in accordance with the present disclosure has an essentially circular cross section, the nominal diameter of the cross section of circumference C is 100-1,000 μm. When referring to blades resembling in their configuration a file (e.g. made of diamond dust), cutting edges 214 extend to a level of Ra being in average between about 2-100 μm.

FIG. 2B illustrates the transverse cross section of the device 200 along the line W-W in FIG. 2A. The dashed line represents the circumference C which is the circumference of the segment 206 outside depression 208. Also shown are the blade edges 214 which extend peripherally and beyond the circumference C. It is noticed that in this particular embodiment, blades 212 may also be defined as having a base end 232 that does not necessarily merge with circumference C and may extend beyond C. Further notably, the dimensions of blades 212 and distances between blades 212, are not necessarily identical and may vary in shape and size and space there in between, depending, inter alia, on manufacturing process of the material constituting the blades.

Figure 3A:
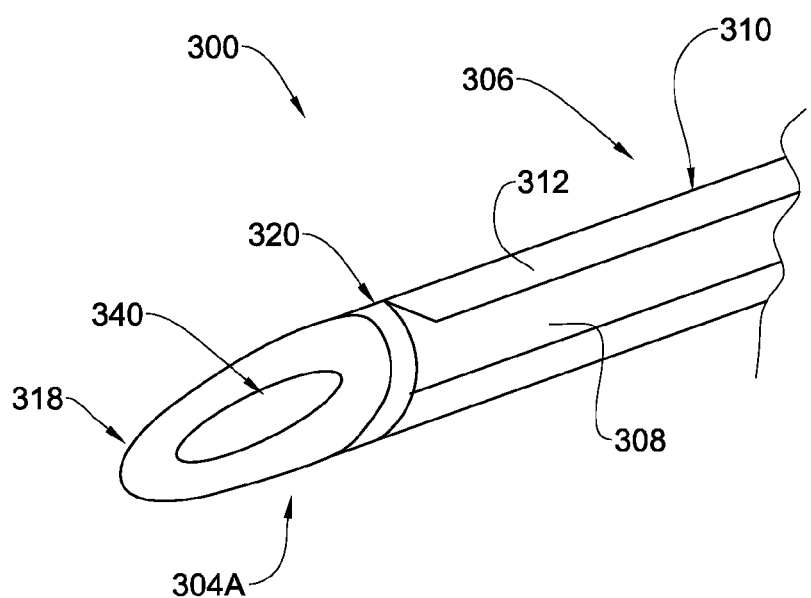
FIGS. 3A-3C are isometric views of a second end with a piercing tip according to alternative, non-limiting, embodiments of the present disclosure.
Figure 3B:
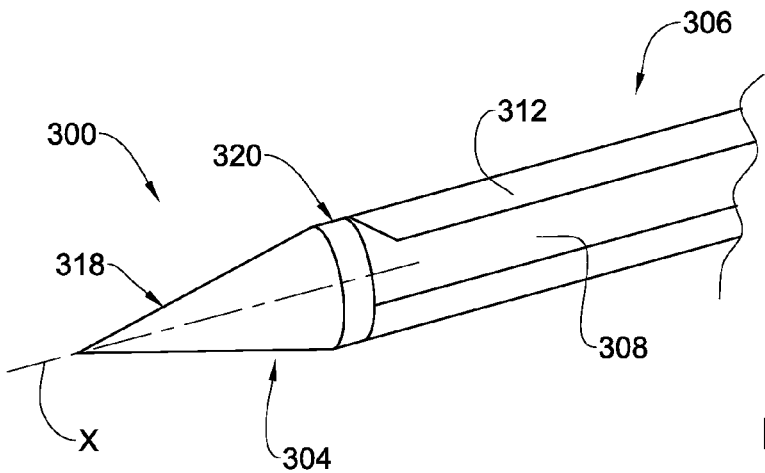
Figure 3C:
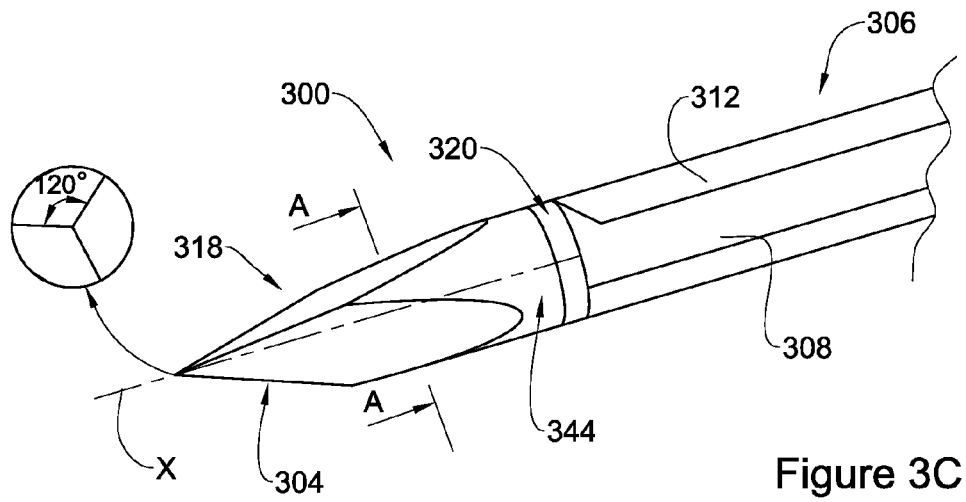

Second end 104 in FIG. 1A or 204 in FIG. 2A is configured to assist in directing the device disclosed herein into a target soft tissue, and to easily pierce and penetrate into the soft tissue. As such, other configurations for the second end are applicable as illustrated in FIGS. 3A-3C. For simplicity, reference numerals similar to those used in FIG. 1, shifted by 200, are used to identify components having a similar function in FIGS. 3A-3C. For example, element 304 in FIGS. 3A-3C is a second end having the same function as second end 104 in FIG. 1.

In FIG. 3A a portion of device 300 is illustrated showing elongated body 306 with a second end 304 in the form of the prevalent piercing tip 318 of a medical needle comprising a lumen 340 sealed at gap section 320. Also illustrated in device 300 is a blade 312 extending peripherally from circumference 310 and a depression 308. When using a needle like tip which has a lumen, sealing may be an integral part of the elongated body, or be created by welding a barrier from the same or different material forming the elongated body, or sealing may be provided using conventional and biocompatible/curing materials, such as, but not only, one or more epoxy resins. At times and in accordance with this embodiment, the entire device is constructed on the basis of a medical needle, with a depression formed by creating a dedicated longitudinal slot along the needle to form the desired depression(s) with the one or more blades being connected at the edge (rim) of the slot. Details about manufacturing processes follow below.

In FIG. 3B a portion of device 300 is illustrated with an elongated body 306 having a circular cross section as in FIG. 3A, with a second end 304 in the form of a right cone with the piercing tip 318 and gap section 320. Also illustrated in device 300 is a blade 312 extending outwardly from circumference C and a depression 308.

In FIG. 3C, a portion of device 300 is illustrated with an elongated body 306 having a circular cross section as in FIGS. 3A and 3B, a piercing tip 318 and a gap section 320. The second end 304 has an equilateral triangle cross sectional shape along line A-A that extends from piercing tip 318 to transition section 344 that converges with gap section 320, the latter having a circular cross section. At times, the shape of second end 304 according to this embodiment is referred to as the "Mercedes" shaped end, with an angle of 120° between the three faces of the triangle. Also illustrated in device 300 is a blade 312 extending outwardly from circumference C and a depression 308.

Different shapes of a second end for a device in accordance with the present disclosure have been taken into consideration, along with the needed force for easier and less painful penetration into soft tissue such as the sclera in the eye. As described herein below, the force applied was compared to the force needed when a regular gauge 25 hypodermal needle with an outer diameter of 0.5 mm was used. Three different tip types were investigated, a conical tip as in FIG. 3B, a triangular cross sectional tip (Mercedes-like) and a rectangular cross sectional (4 phases) tip (not illustrated), when all having a 5°-15° head tip angle α. The experiment results showed that the force applied with the Mercedes-like shape gave the best results for the purpose of cutting and penetrating soft tissue such as the sclera.

As appreciated, bearing in mind that the second end is configured to ease penetration of the device into soft tissue and the fact that not only one kind of soft tissue exists, many other designs for the second end may be equally applicable. Thus, the present disclosure should not be limited by the individually exemplified embodiments for said second end.

Figure 4:
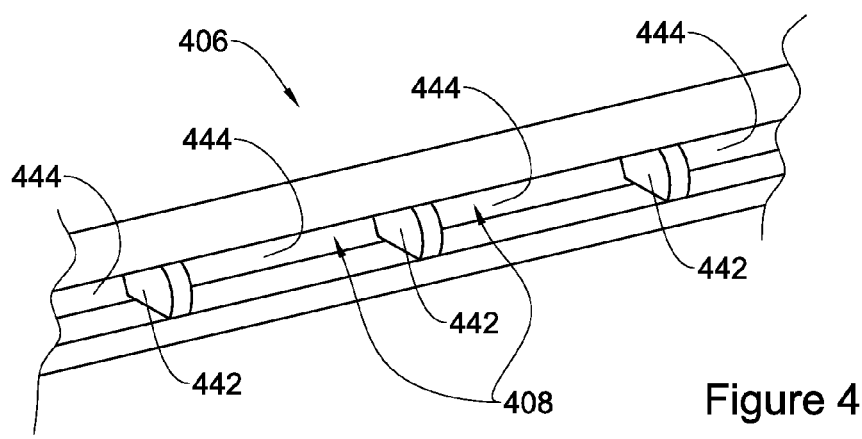
FIG. 4 is a schematic illustration of a depression in a device, with a plurality of partitions dividing the depression into compartments; according to some embodiments of the present disclosure

Referring to FIG. 4 there is illustrated a portion of a device's segment 406 with three spaced-apart partition walls 442 dividing depression 408 into, respectively, four compartments 444. It is to be understood that while three partition walls are illustrated, the depression may similarly consist of only one, or two or even more than three partition walls. Partition walls 442 are typically, albeit not exclusively, included in order to form barriers that prevents the flow of fluid through depression 408 from one side to another side of the device. For example, if the device is used to cut sclera tissue of the eye, partition walls 442 prevent fluid from flowing from the internal chamber of the eye towards outside of the eye.

It is to be appreciated that while the partition walls are illustrated in this embodiment as full partitioning walls, i.e. extending along the entire inner perimeter of the depression, the walls may also extend, like a pillar, from only part of the inner surface (to provide partial partitioning with compartments only partially separated one from the neighboring compartment). This construction may allow, during operation, for matter collected in the depression to cross from one compartment to another during operation.

In FIGS. 5A-5B additional possible alternative features for a device according to the present disclosure are provided. It is to be appreciated that the additional features in FIGS. 5A-5B need not to be used together and each feature should be considered as a separate possible feature that may be added to the elements of the device hitherto described. Similar to preceding FIGS. 2 to 4, reference numerals similar to those used in FIG. 1 or 2, shifted by 400 or 300, respectively, are used to identify components having a similar function in FIGS. 5A-5B. For example, element 512 in FIG. 5A is a blade having the same function as blade 112 in FIG. 1.

Specifically, FIG. 5A illustrates, isometrically, a portion of device 500A with a blade 512 extending outwardly from circumference C and a depression 508, all being similarly shown in FIGS. 1 to 4. However, FIG. 5A also illustrates an elongated hump-like protrusion, referred to as ridge 546 positioned over at least part of external surface 510 of segment 506, and typically, in parallel albeit on opposite side of depression 508. In operation, ridge 546 may assist in stretching tissue surrounding the external surface thereby ensuring that tissue is in contact with cutting edge and a layer thereof is cut during rotation (under stretch). The dimensions of ridge 546 are important factors for determining the level of stretching exerted on the tissue. In general, the greater the ridge's apex "H" is distanced from the contour of the external surface, the greater is the tissue stretching. A balance needs to be maintained in order to, on the one hand, increase contact between the tissue and the blade, e.g. by such stretching means, and on the other hand, minimize any inconvenience or pain that may be caused to the treated subject or even affect performance of the device during operation. According to some embodiments, the dimensions of ridge 546 are defined by an apex having a height "H" as shown in FIG. 5A, and being perpendicular to the external surface of the segment, where H is no more than 10%-50% of the dimension of diameter Di.

Further illustrated in FIG. 5A, depression 508 also comprises a barrier 550, in this embodiment, illustrated as an inner wall extending inwardly along the depression. The barrier 550 may be one continuous wall (as illustrated) or a series of individual walls. The barrier 550 may assist in controlling the amount/volume of matter (e.g. tissue) collected in the depression. In other words, the barrier acts as a compartment or depression size reducer. In some embodiments, the barrier is fixedly attached to the depression, and in some other embodiments, it is removably placed within depression 508, e.g. by dedicated gripping seat (not illustrated).

The shape of barrier 550 may be simply rectangular or any other suitable shape. While rotating the device, tissue will gradually enter depression 508 until it reaches barrier 550, preventing from additional tissue to enter into the depression, probably by that terminating the cutting process by the blade 512. Without being bound by theory, it is assumed that once the depression is filled with the desired volume of tissue, blade 512 trims off the tissue layer from the surroundings.

In order to control the depth of insertion of the device into tissue, the device may include a blocking member, or stopper 552 circumferencing external surface 510 at or proximal to first end 502, preferably, where there is no depression. The blocking member 552 is typically used to prevent penetration of the device beyond a desired depth within the treated tissue. To this end, and in accordance with some embodiments, blocking member 552 is fixed in place proximal to said first end. However, in accordance with some other embodiments, blocking member may be configured such to slideably be displaced along the elongated member 506, e.g. to be lined with a partition wall. The blocking member 552 may also assist in supporting orientation and promote stabilization of the device once being penetrated into the tissue.

The blocking member 552 may have different shapes and configurations. In the illustrated embodiment, the blocking member is in the form of a gradual increase in the diameter of the elongated body (resembling a belt overlaying circumference C), at the junction between the segment 506 and the first end 502. The blocking member prevents the device from entering the tissue beyond the blocking member 552 location. Alternatively, the blocking member 552 may be created by firmly fitting a flexible band over the elongated body at the desired location in the first end. The blocking member 552 illustrated in FIG. 5A may be made from the same material of the elongated body, e.g. stainless steel or ceramic material (Tungsten Carbide), or from any other suitable material. At times, the blocking member 552 has dimensions that prevent the elongated body from further penetrating one tissue, but does not prevent penetration to another tissue. As will be further discussed below, when creating a channel in the eye, a blocking member may be such to allow penetration through the conjunctiva of the eye, but prevent excess penetration of the elongated body via the sclera.

In FIG. 5B, a device 500B, similar to device 200 is shown, albeit with a barrier in the form of a protective shaft 560, having, in this embodiment, a hollow cylindrical shape. Device 500B is entered from its first end 502 through the lumen of protective shaft 560.

When in operation, namely, the elongated member extending between a first end 502 and a second end 504 constituting a tissue piercing tip, and a segment 506 extending from the second end 504 is rotating, protective shaft 560 is static, and by this it protects the surrounding tissues from being damaged during the rotation of the elongated member. This is useful, for example, in operating on the eye, so as to protect the conjunctiva that surrounds the sclera. In one embodiment, the protective shaft may be fixedly attached/interlocked to a grip unit, to which the device is also attached by engagement element 516, by its back side 562. It is to be noted that protective shaft 560 may also function to block the device from being excessively entered into the soft tissue in a manner similar to blocking member 552 in FIG. 5A. Protective shaft 560 may also be configured to be slidably positioned at a certain position relative to the piercing tip, so that it defines the length of the functionally cutting segment of the device, and by this allowing to adjust the device to the relevant tissue meant to be cut. Notably, while FIG. 500B illustrates a device similar to device 200 in FIG. 2A, a protecting element of this type may similarly be used with a device including an elongated blade, such as that illustrated in FIG. 1A.

Figure 6A:
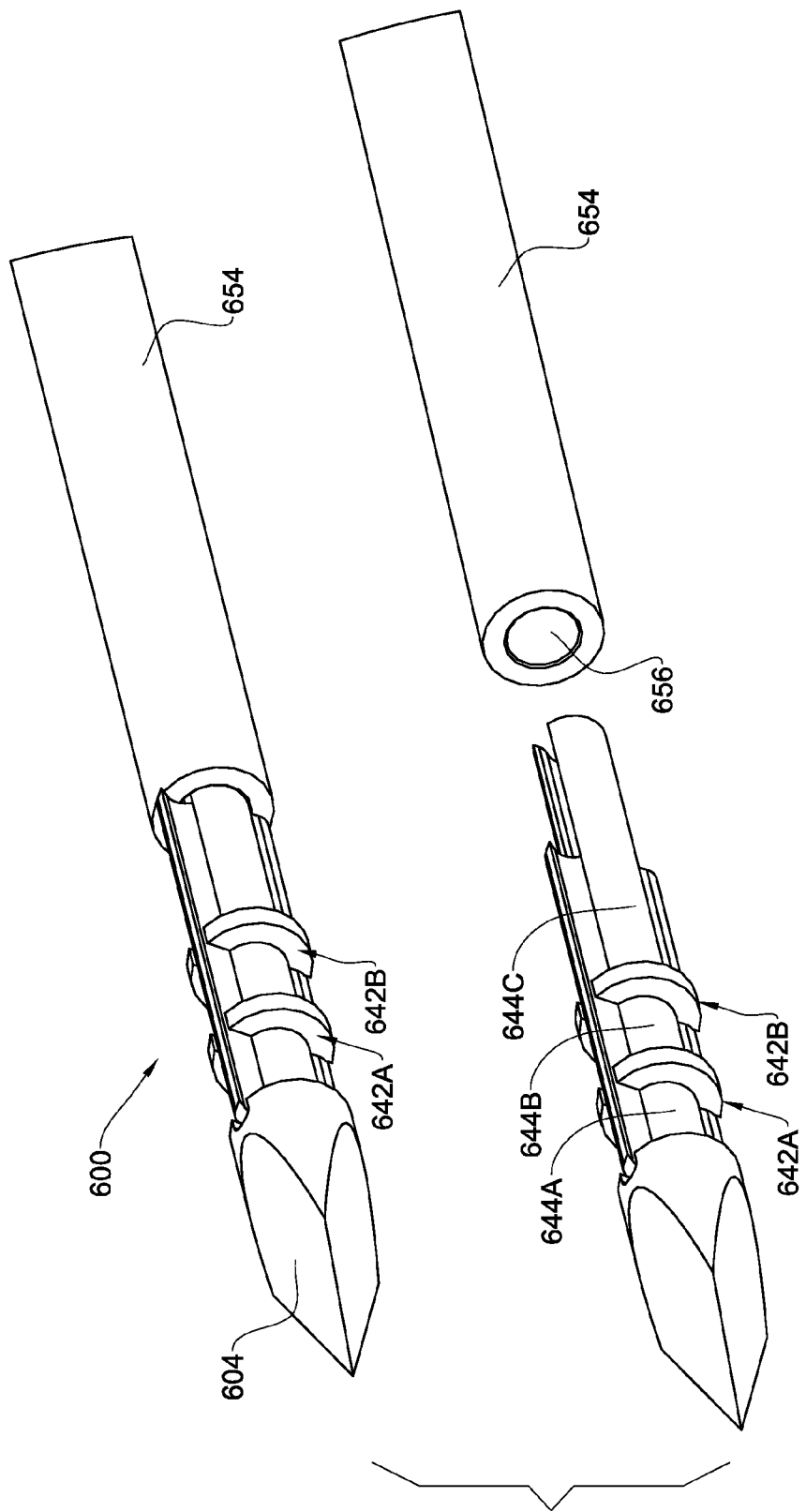
FIGS. 6A-6D are illustrations of devices according to some more embodiments of the present disclosure with FIGS. 6A and 6B providing isometric views and FIG. 6C providing a cross sectional view of a device in accordance with one embodiment, and FIG. 6D providing an isometric view of a device in accordance with another embodiment.
Figures 6B, 6C:
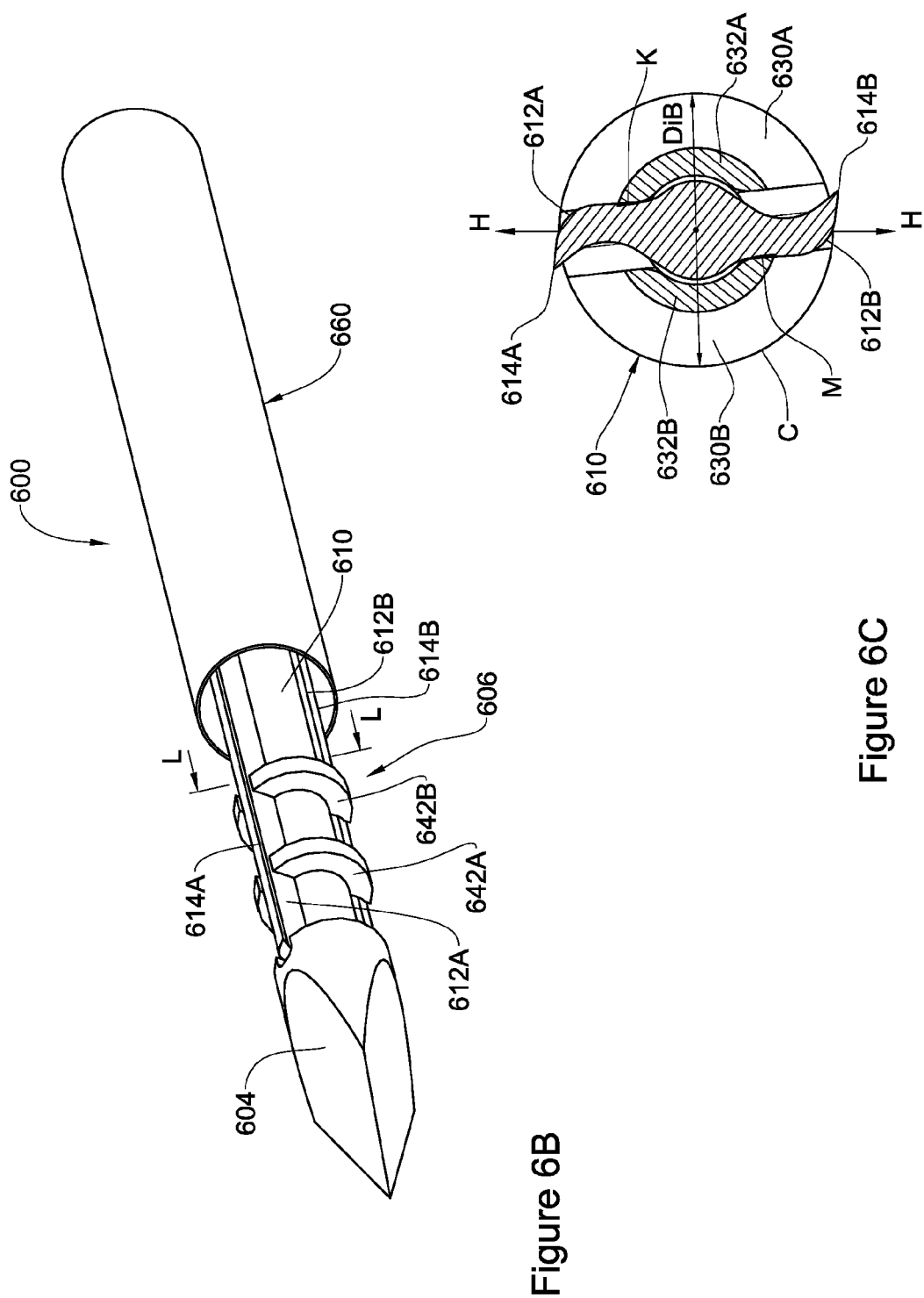
Figure 6D:
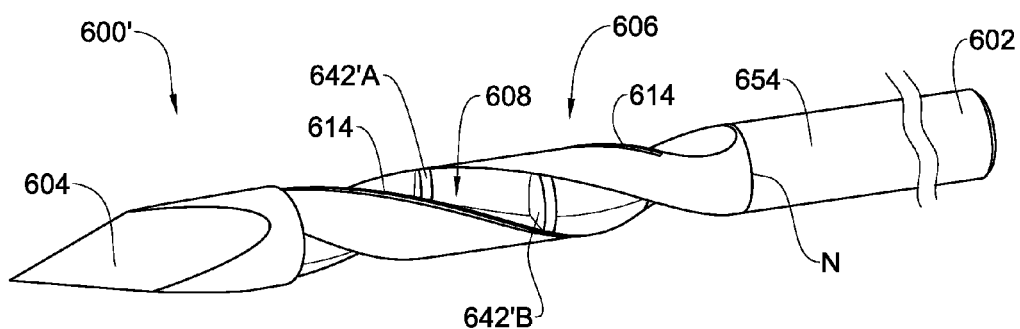

FIGS. 6A-6D are illustrations of devices according to some embodiments of the present disclosure with FIG. 6A-6C providing views of a device in accordance with one embodiment, and FIG. 6D providing an isometric view of a device in accordance with another embodiment.

Reference is now made to FIGS. 6A-6C, showing a device 600 in accordance with another embodiment of the present disclosure. For simplicity, like reference numerals to those used in FIG. 1, shifted by 500 are used to identify components having a similar function. For example, component 604 in FIG. 6 is a first end having the same function as first end 104 in FIG. 1.

Specifically, in FIGS. 6A-6B, a segment of device 600 is shown including a second end 604 having a triangular cross section (Mercedes shape). Along segment 606 there are two blades 612A and 612B having edges 614A and 614B respectively. Also, the device comprises two partition walls 642A and 642B that embrace segment 606 (like belts) and function as barriers for fluid movement from second end 604 towards the first end (not shown). In this non-limiting example, three compartments, 644A, 644B and 644C are formed between partition walls 642A and 642B. The three compartments define depressions and during rotation, tissue that is cut by blade(s) may be stored in these compartments. The depressions may be defined by their volumes, or their internal diameter, which may be dictated by the dimensions (diameter) of the channel to be created inside the tissue.

The elongated part of device 600 includes the cutting segment which extends from the second end 604 and is connected to an elongated rod 654 having generally a smooth and circular surface, the elongated rod extends the length of the device so that to enable mounting it on a grip rotating unit from the first end (not shown) of the device. The elongated rod is usually a cylinder being full or hollow. Being configured as full the rod can withstand more stresses and torque. In case it is full, the rod 654 will have, as shown in FIG. 6A, a dedicated inlet 656 to enable connecting it to the cutting segment of the device. As shown in FIG. 6B, device 600 may be inserted from its first end into a protective shaft 660 having the same functions as described with regards to protective shaft 560 in FIG. 5B. Like blocking member 552, the protective shaft 660 may function as a stopper that prevents device 600 from excessive penetration into soft tissue. For example, when using the device inside the eye to create a channel in the sclera, it is important that the device does not penetrate to an extent that causes damage to the inside of the eye. Protective shaft 660 can be positioned at a preferable distance from the second end revealing the desired length of the cutting part extending along segment 606.

It should be noted that while this example includes only two cutting blades along segment 606, it is equally possible that segment 606 comprises a plurality of blades forming a fan-like cross sectional shape.

A cross section along line L-L in segment 606 is illustrated in FIG. 6C. Segment 606 has a circular external surface 610 with a circumference C. Line H-H defines two sides (halves) of device 600, where each side includes two parts, parts 630A and 632A defining a first side and parts 630B and 632B defining a second side. Parts 632A and 632B are fixedly attached (e.g. welded, glued, anchored) to the elements holding the blades, at K and M, as shown. External surface of segment 606 may be defined by a diameter DiB. In some embodiments, diameter DiB has a nominal value of between 100-1,000 μm, depending on the particular application of the device, e.g. at different parts or organs of the body and/or in different species.

In FIG. 6D, an isometric view of device 600' according to another embodiment of the present disclosure is shown. The device 600' has a second end 604 with a triangular cross section (Mercedes shape). While the Mercedes shape in the second end is a preferred embodiment, it should be understood, that the second end may have any of the configurations illustrated above in relation to FIGS. 3A-3C, or any other configuration suitable for piercing soft tissue. The device 600' also has an elongated rod 654 having the same functions as detailed above with regards to device 600. The segment 606 (which includes the cutting part responsible for cutting and collecting the cut tissue) may be integrally formed with the elongated rod 654 or attached thereto at N.

As further shown in the figure, segment 606 (including the cutting part) has several spiral depressions 608 found between several spiral blades with cutting edges 614 extending along the longitudinal axis of the segment 606. During the rotation of device 600', the cutting edges cut the surrounding tissue which is then received in the depressions between the cutting edges.

Optionally, device 600' may include one or more partition walls along each spiral depression 608. In the example of FIG. 6D, two partition walls 642'A and 642'B are shown along one of the depressions. These partition walls are intended to function, at least, as fluid barriers (similar to two partition walls 642A and 642B in FIGS. 6A and 6B), for preventing the flow of fluid through depression 608 from one side to another side of the device 600'. In particular, this may be useful when using device 600' for creating a channel in the eye wall, in order to prevent the fluid inside the internal chamber from escaping the eye through the depressions in the device.

The devices subject of the present disclosure, including those illustrated in FIGS. 1 to 6, are preferably disposable. This makes working with these devices more convenient and sterile, not requiring service prior to usages.

Figure 7:
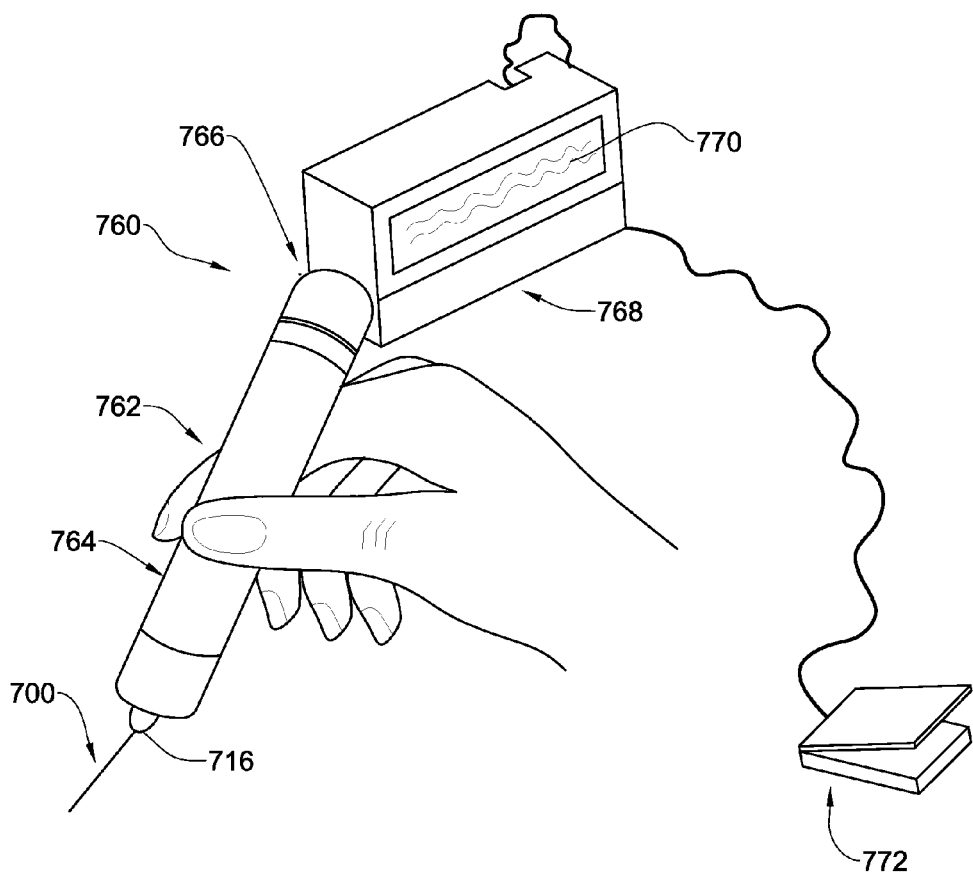
FIG. 7 is a schematic illustration of a device according to an embodiment of the present disclosure and being engaged with a rotor to be used for cutting soft tissue.

Reference is now made to FIG. 7 illustrating the device when connected to a rotor to form an assembly in accordance with the present disclosure. Again, for simplicity, same reference numbers, shifted by 600 or 500 are used to describe similar elements shown in FIG. 1 or FIG. 2 respectively. Specifically, the assembly 760 comprises a device 700 engaged within a grip unit 762 comprising a shank 764 to enable holding the device 700. The shank 764 is connected to the device via a rotatable engagement part 716 the rotation of which being operated by a rotor 766 within the grip unit 762. Rotor 766 may be operated by a motor or manually (e.g. using a spring). The operation of the rotor may be controlled by a control unit, in this embodiment control unit 768, for defining and selecting various parameters relevant to the effective actuation of the rotatable part 716, and effective operation of the assembly. The control unit may form part of the grip unit 762 or may be a remote part thereof, connected to the grip unit with a wire or wirelessly. Some of these parameters include, without being limited thereto, On/Off switching of the rotor, speed of rotation, number of rotations, and control over reciprocal movement of the device. The control unit 768 may comprise a control panel 770 including a user interface for selecting the desired parameters.

According to some embodiments, the grip unit 762 may be powered and actuated electrically. In other embodiments the force of rotation may be mechanic, such as using a spring that causes torque and results in rotation of the rotatable part 716.

Yet, at times, to actuate the rotor 766 and hence the rotation of the device, medical assembly 760 may also comprise a pedal 772 connected through a wire 774 or wirelessly to the rotor or to the control unit 768, such that upon pressing pedal 772 the device is actuated and rotated according to the parameters that were chosen through control unit 768.

In operation, the device is used to excise soft tissue, typically, biological soft tissue (i.e. biological tissue, other than bone which is considered hard tissue). Removal of soft tissue may be for example, for biopsy, but also for creating voids or channels within the tissue.

In one aspect, the device is operable to provide a method for excising soft tissue from a living body, the method comprising:
  (i) providing a medical assembly comprising a grip unit operably connected to a device disclosed herein;
  (ii) piercing biological soft tissue at a location where tissue removal is desired, with a piercing end of the device, and sliding the device into the soft tissue to a desired depth within the soft tissue;
  (iii) actuating rotation of the device while being embedded in the soft tissue to allow at least one full rotation of the device about its longitudinal axis, during said rotation soft tissue is cut around an external surface of the device and is received in at least one depression of the device;

(iv) upon termination of rotation, removing the device from the soft tissue, leaving a channel within the tissue, the dimensions of the channel being dependent on the amount of tissue removed.

The extent of sliding, or in other words, the depth of insertion of the device into the soft tissue may be controlled or monitored using the scale markers and/or the positioning of the blocking member and/or the position of the protective shaft.

During rotation, if a device with elongated blades, such as the device of FIG. 1, is used, a circular layer or slice of tissue around the external surface of the segment is cut. Alternatively, if using a device with a cutting produced by the roughness of the surface, e.g. using diamond dust, such as device 200 illustrated in FIG. 2, tissue is removed in the form of debris scraped from the live tissue.

As may be appreciated, due to rotation of the device about an axis, after withdrawal of the device from the body, an essentially symmetrical tubular channel is formed within the body, the diameter of the channel being approximately 2*DS in the case of a device 100 illustrated in FIG. 1. If more than one rotation is performed, additional layer of thickness DS or less is cut and removed to eventually form a channel proportional to the number of rotations, and being equal or less than 2n*DS (n being an integer representing the number of rotations about axis X). If a device such as device 200 in FIG. 2 is used, the diameter of the final channel depends on the number of rotations and at maximum it may reach 2*Ra, assuming that all the valleys will be filled with tissue debris. At any rate, in the context of the present disclosure, when referring to the diameter of the channel created it is to be understood as referring to the diameter after recoiling of the tissue in the channel.

In some preferred embodiments, the device and assembly are used to reduce intraocular pressure, by forming a thin draining channel along the sclera and/or cornea tissue.

The intraocular pressure (IOP), is the leading cause of glaucoma, the latter relating to a group of eye disorders that may cause damage to the optic nerve which may result in the development of blind spots in the visual field and even irreversible blindness, in case the whole optic nerve is destroyed. Thus, in order to prevent development of glaucoma or glaucoma progression, there is a need in the art to develop means for reducing intraocular pressure.

Figure 8A:
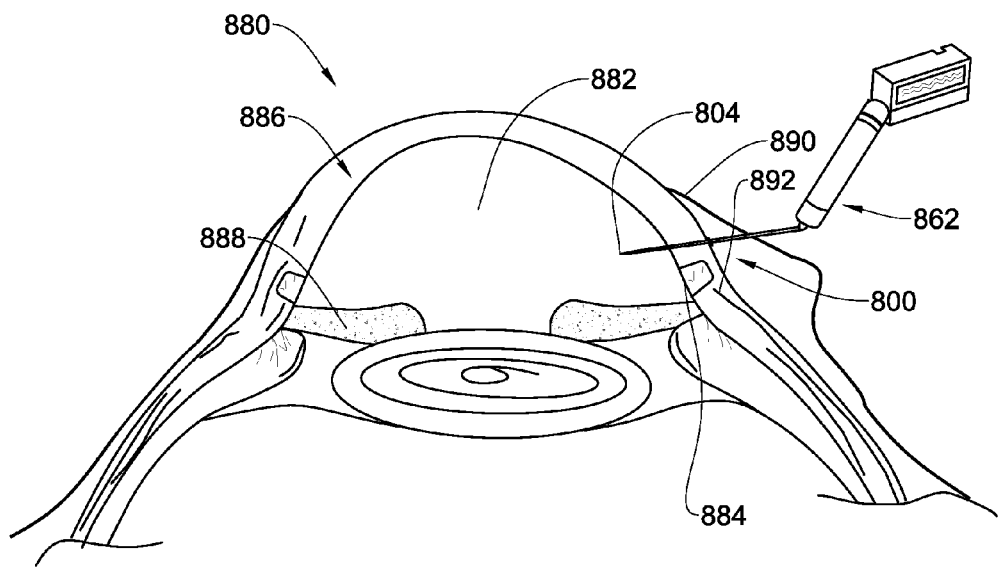
FIGS. 8A-8B are schematic illustrations of a device embedded in the wall of the eye, for use in creating a channel within the sclero-corneal junction area of the eye in accordance with an embodiment disclosed herein, with FIG. 8B representing a magnified portion of FIG. 8A.
Figure 8B:
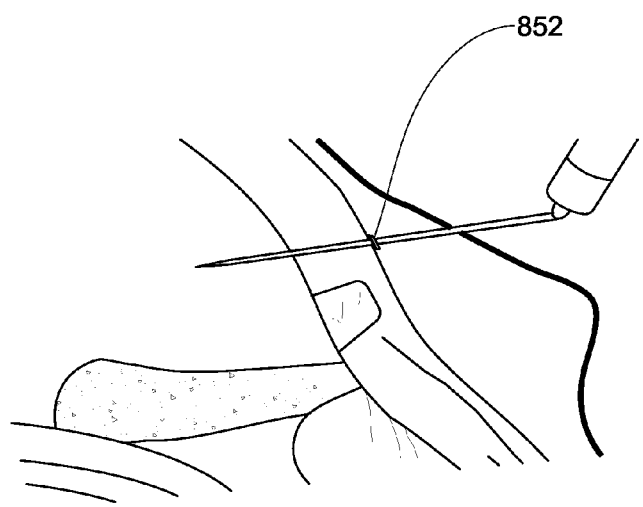

Referring now to FIGS. 8A and 8B, there is illustrated a portion of a cross section of an eye 880 of a human being (FIG. 8B being a magnified portion of the eye of FIG. 8A). Under normal conditions, aqueous humour flows continuously in and out of the anterior chamber 882 maintains the IOP and nourishes the nearby tissues. The fluid leaves the anterior chamber 882, through a meshwork 884, at an open angle where the cornea 886 and iris 888 meet.

Excessive IOP is caused by decreased drainage of the fluid from the anterior chamber of the eye and current treatments include medicinal drugs, laser treatment (trabeculoplasty), or surgery (trabeculectomy or drainage implant).

For the purpose of reducing intraocular pressure, there is thus provided a method comprising creating a channel (drainage channel) in the wall of the eye at or close to the junction between the sclera and cornea (herein the "sclero-corneal junction"). It should be noted that the channel may be created totally within the sclera or partially within the sclera and cornea. The channel typically extends from the anterior chamber of the eye to the interface between the sclera and the conjunctiva. The drainage channel after recoil of the tissue has an internal diameter of no more than 200 µm, preferably between 20 µm and 200 µm, or between 100 µm-200 µm.

In this context, the device 800 according to the present disclosure is used to form a drainage channel of controllable size for release of fluid accumulated in the anterior chamber 882 and thereby reducing the IOP. It has been found by the inventors that a diameter of a channel greater than about 200 µm after tissue recoil, e.g. 1,000 µm, would cause collapse of the eye (probably due to excessive leakage of the fluids from the anterior chamber of the eye).

The conjunctiva 890 is lifted from the sclera 892 by a physician, or any other skilled person in the art, using for example a surgical forceps. Then, the conjunctiva 890 is pierced with the piercing second end 804 of the device after which the device is gently forwarded into the sclera tissue 892 which is then pierced by the piercing second end 804 in the limbal area, again close to where cornea 886 and sclera 892 meet. The lifting of the conjunctiva ensures that the eventual piercing hole in the conjunctiva and in the sclera do not coincide, thereby ensuring that no post treatment leakage of aqueous humour would occur. The device 800 is pushed forwards towards and through the sclera 892 in a direction almost parallel to iris 888, forming a small angle with the cornea's outer surface.

The scale marks on the device's surface, the blocking member and/or the protective shaft (not illustrated in FIG. 8) assist in ensuring that the device is inserted only up to the desired depth thereby minimizing any potential damage to the internal portion of the eye. At times, the device 800 can be viewed through the transparent cornea, which may also assist in preventing unintentional excessive insertion of the device into the eye. To this end, scale marks may be present on the second end and on the gap section of the device such that once they are viewed via the transparent cornea, the physician will know to stop pushing the device further into the eye. Moreover, a blocking member 852 of the device assists in controlling the distance that the device 800 can penetrate the eye. The blocking member 852 can also be configured like protective shaft 660 described in FIG. 6B. In operation, device 800 is inserted until the sclera surrounds the cutting portion of the device (segment 806 with the at least one elongated blade or the file-like rough surface configuration or any other configuration in the context of the present disclosure).

When a channel is to be created in the eye of a human subject, the length of second end would be in the range of 200 µm to 4,000 µm and the length along axis X including the second end and the gap section would be in the range of 2,000 µm to 5,000 µm. The length of the cutting portion would be between 2,000 µm and 3,000 µm.

Further, when a channel is to be created in the eye, it is preferable that the gap section is sealed. This would assist in minimizing undesired leakage of fluid from the anterior chamber of the eye during the initial piercing of the tissue. Once the cutting segment is situated properly inside the eye wall, i.e. inside the sclera or the sclero-corneal junction, the grip unit 862 is actuated via the control unit (not shown) causing the device to rotate around its longitudinal axis X, at a speed and for a number of rotations that are a priori selected by the physician operating the device, e.g. via its control unit (It should be clarified that the grip unit 862 as shown is not in scale with the eye portion in the Figure, and its only purpose is to illustrate its possible position relative to the eye). As already was explained, the number of rotations dictates the diameter of the channel formed within the eye wall (the eye wall comprising sclera tissue, cornea tissue or both), in the case that device 800 is similar to device 100 the diameter being proportional to DS, which is the distance between the blade's cutting edge and the external contour of circumference C, and if the device 800 is configured like device 200, the diameter of the channel is related to Ra explained above. Once the desired amount of tissue is collected in the device 800, or the desired amount of rotations are performed, rotation is terminated, and the device is gently pulled out of the eye, carrying within it an amount of scrapped sclera/cornea tissue, leaving within the eye wall a channel with a desired diameter. This channel provides a drainage path for aqueous humour from the anterior chamber to the space between the sclera and the conjunctiva thereby reduce IOP.

Initially, a bleb will form under the conjunctiva 890 by the fluid which exits through the channel. It is good to notice that the fluid will not leave the eye through the conjunctiva 890, as the slit in it is far from where the bleb is formed (immediately above the channel). In this way, the drainage is controlled and the extra fluid is carried away via the blood vessels of the eye.

According to some embodiments, the area in the vicinity of the formed channel is treated with a suitable anti-scarring agent, such as mitomycin-C (available commercially, e.g. as Mitosol, Mobius Therapeutics), to minimize any scar development which may clog the open channel. The area may be defined as the space between the conjunctiva and the sclera, at the eye quadrant where the channel is formed.

It will be appreciated by persons of ordinary skill in the art that the exact locations where the conjunctiva and the sclero-corneal junction area are pierced are not restricted to what has been described, and every case should be considered individually.

The device, medical assembly and method disclosed herein are not limited to human treatment. In fact, the device may be equally designed (particularly in terms of dimensions) to be suitable for treatment of other living beings, such as dogs, horses, cats. The main difference would be in the dimensions of the device. The differences in the devices, depending on the treated species, may reside in the dimensions of the devices' segment, length of the first and second ends, the circumference C and diameter Di of the device, the dimension/volume of the depression and the value of the effective cutting thickness DS.

The device may be manufactured according to procedures known to those skilled in the art. For Example, and without being limited thereto, the second end (the piercing end) may be created by techniques typically used for manufacturing needles or by electrochemical sharpening. For the depression, one may use a commercially available cannula (hollow tube), e.g. of a needle, or using techniques such as electrical discharge machine (EDM). The blade may be formed as an integral part of the elongated member, or may be welded to the member, using for example, spot-laser welding. Similarly, the barriers within the depression or outside external surface (FIG. 6A) may be welded or integrally formed with the device. The material from which a device may be made can be stainless steel or ceramic material (Tungsten Carbide).

Figure 9A:
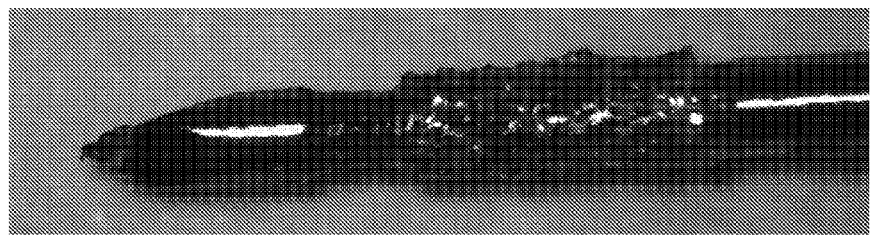
FIGS. 9A-9D are images of steps of manufacturing a device in accordance with an embodiment of the present disclosure.
Figure 9B:
Figure 9C:
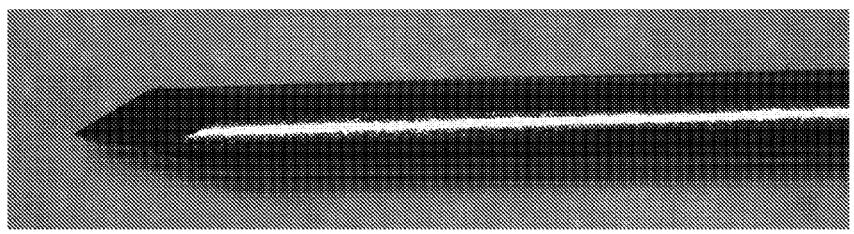
Figure 9D:
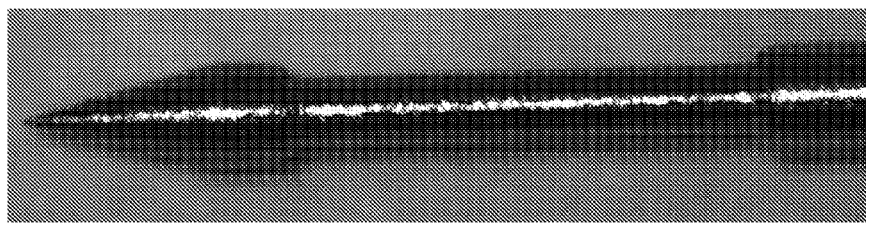

Referring to FIGS. 9A-9D there are provided four exemplary devices. FIGS. 9A and 9B provide images of device manufactured in accordance with principles of the present disclosure, i.e. after diamond electro plating to obtain a diamond dust cutting surface, the two devices being different in the roughness of the surface created by the diamond dust coating. FIG. 9C illustrates a device with only a Mercedes-like second end and no cutting blades, while FIG. 9D exemplifies a device where the second end has a conical shape and while with a dedicated depression, the device is without blades.

Figure 10:
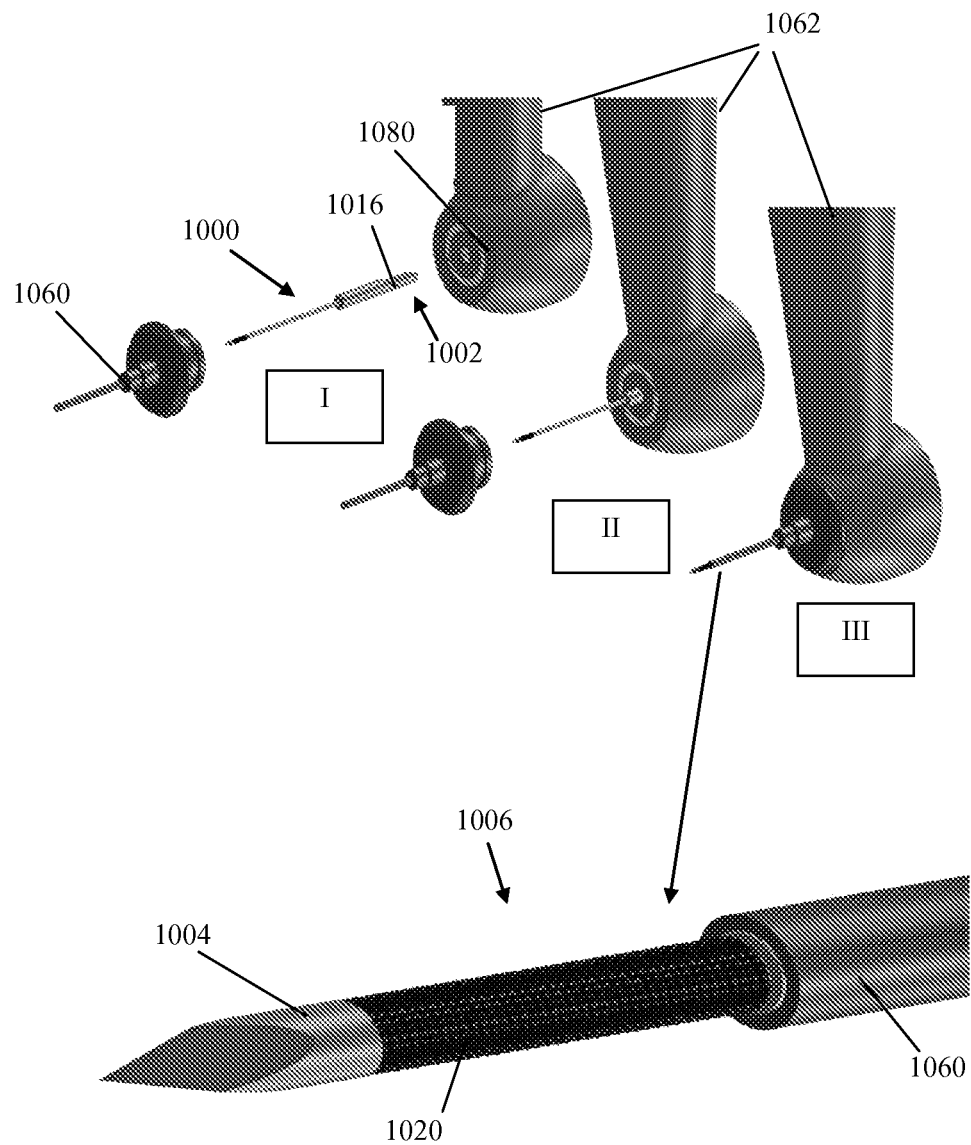
FIG. 10 illustrates stages of assembling components of a device in accordance with a non limiting embodiment.

FIG. 10 provide stages of assembling components of a device in accordance with the present disclosure and rotating mechanism. For simplicity, like reference numerals to those used in FIGS. 6A-6B, shifted by 400 are used to identify components having a similar function in FIG. 10. For example, component 660 in FIG. 6A is a protective shaft having the same function protective shaft 1060 in FIG. 10.

Specifically shown in FIG. 10 is a device 1000 having a first end 1002 containing an engagement element 1016 which in this case has an interlock engagement mechanism, and a grip unit 1062 that includes a rotating mechanism to cause rotation of the device 1000 around its longitudinal axis. Also shown in FIG. 10 is a protective shaft 1060. Protective shaft aids also in stopping the device from penetrating the eye beyond the safe level. Initially, as illustrated in stage [I], device 1000, protective shaft 1060 and grip unit 1062 are separated. In stage [II] device 1000 is interlocked with the grip unit 1062, via inlet 1080, while protective shaft 1060 is still separated from the assembly. Then, protective shaft 1060 is sled over the device and firmly attached to the grip unit holding the protective shaft 1060 in static state, such that when the device is rotated no movement of the protective shaft occurs. Stage [III] shows the three components together in a state ready for activation. A zoom-in of the device 1000 with the protective shaft 1060 is further shown, including its second end 1004 which includes a Mercedes-like piercing tip, a gap section 1020, a cutting segment 1006 including a plurality of blades, i.e. in the file-like model (e.g. from diamond dust).

Non-Limiting Examples

Evaluation of a Device as Shown in FIG. 10

Figure 11A:
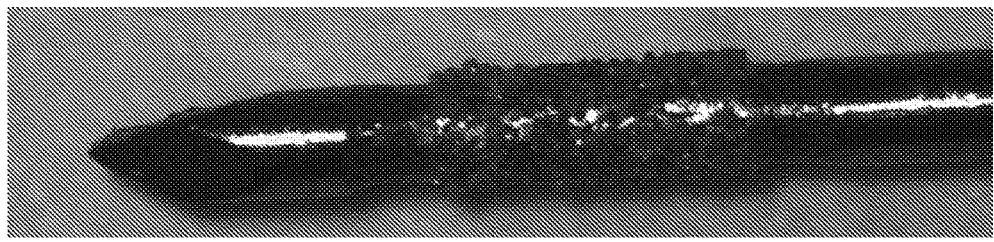
FIGS. 11A-11C are images of stage in the formation of a sclera corneal channel using a device in accordance with an embodiment of the present disclosure.

A device as shown in FIG. 11A was used to create a drainage channel in an eye of a pig cadaver at sclera-corneal junction using a file-type device as shown in the figure. The file was achieved using diamond plating. Further, the device had a Mercedes-like piercing tip.

Swine eyes were supplied by the official authority. The conjunctiva tissue was removed by a surgeon in order to allow easy approach to the sclera-corneal junction.

After the conjunctiva tissue removal, the device was inserted into the eye's wall. During rotation (according to a predefined RPM and duration) there was an interaction between the device and the sclera tissue and a thin layer of the sclera was removed.

At the end of the procedure, the device was withdrawn from the eye and a drainage channel from the Anterior chamber to the outside the eye was created. Following this, the drainage liquids would accumulate under the conjunctiva tissue, creating a bleb and then getting absorbed into the veins of the eye.

Figures 11B, 11C:
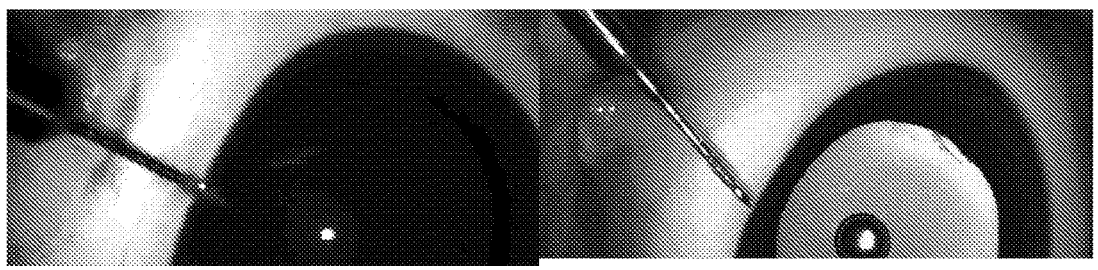
Figure 12:
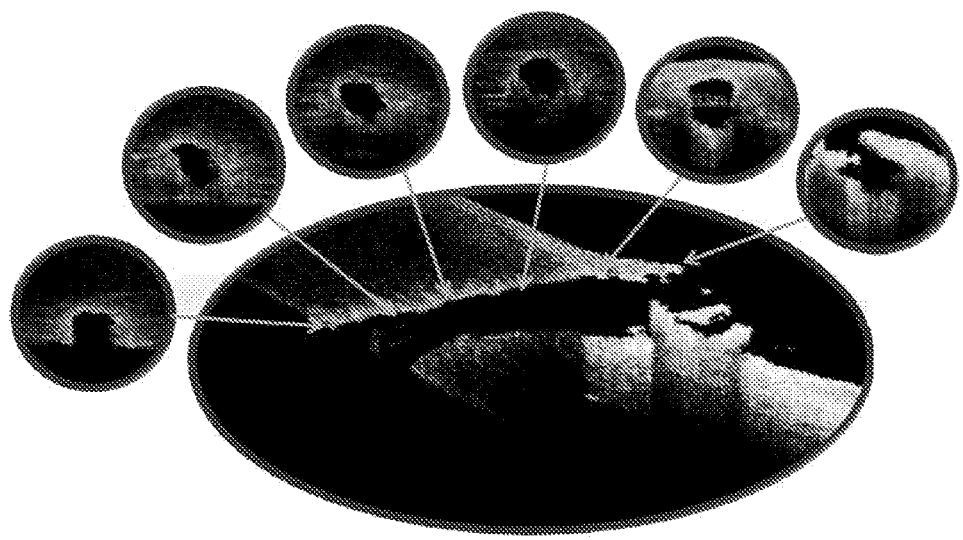
FIG. 12 is an image including cross sectional cuts of a sclero corneal channel performed in accordance with an embodiment of the present disclosure.

FIGS. 11B and 11C show the piercing of the eye and the creation of a sclera-corneal channel by rotating the device shown in FIG. 11A, being attached to a rotating machine at high RPM. FIG. 11B was taken a moment before the piercing was performed, while FIG. 11C was taken after the penetration and a moment before the rotation of the device. By using an Optical Coherence Tomography device the channel created within the sclera of the cadaver eye was imaged immediately after the experiment (before recoil effect of the live eye). This is shown in FIG. 12. The average dimensions of a channel created using the device of FIG. 10.

0.35 mm in diameter and 2 mm length. In FIG. 12, there are shown different sections along the created channel.

In order to prove the effectiveness of the device of FIG. 10 a comparison experiment was conducted between the device of FIG. 10, i.e. with the diamond plated cutting segment, vs. a device having the same piercing end but without the diamond dust plating layer. The results were also captured with an OCT and are shown in FIG. 13A-13B. It is shown that rotating a device in accordance with the present disclosure (FIG. 13A) effectively removed scleral tissue and resulted in an essentially circular contour of the created channel due to tissue removal. Whereas, FIG. 13B shows that when using a device that does not have a diamond plating layer resulted in no tissue removal. As shown in FIG. 13B, the cross section form is a triangle only, as a result of "Mercedes" tip penetration. Subsequent rotation of the simple round rod inside the tissue did not affect the cross section form which remained triangular. On the other side, in FIG. 13A, despite the penetration with a "Mercedes" tip and an expected triangular form, the subsequent rotation have left a circular cross section form due to the interaction between the diamond and the sclera tissue.

Assessment of the effectiveness of the method was carried out by comparing the total real tissue weight removed to the theoretical calculation based on the device dimensions. The removed tissue was scraped from the diamond plated surface, and assuming that the sclera tissue is composed of 70% water and 30% protein, a protein weight analysis was made, using suitable equipment and methods, giving the result that the removed tissue weight is about 48±12 μgr. This was repeated 12 times, and the results are summarized in Table 1 below:

TABLE 1

Protein/Water content of removed tissue

| Sample No. | Protein (μg) | Water (μg) | Total Weight (μg) |
|---|---|---|---|
| 30-5 | 11.69 | 27.28 | 38.97 |
| 46-3 | 15.36 | 35.84 | 51.20 |
| 46-6 | 13.36 | 31.17 | 44.53 |
| 91-1 | 12.89 | 30.08 | 42.97 |
| 91-2 | 22.78 | 53.15 | 75.93 |
| 91-4 | 18.02 | 42.05 | 60.07 |
| 46-8 | 10.47 | 24.42 | 34.88 |
| 54-1 | 15.26 | 35.61 | 50.87 |
| 54-3 | 11.85 | 27.64 | 39.48 |
| 54-4 | 11.42 | 26.66 | 38.08 |
| 54-8 | 17.84 | 41.62 | 59.46 |
| 76-4 | 9.25 | 21.58 | 30.83 |
| Average | 14.18 | 33.09 | 47.27 |
| STD | 3.87 | 9.02 | 12.88 |

On the other, the theoretical calculation was made as follows:

The sclera tissue density was assumed to be 1 gr/ml, according to what is found in the literature.

Given:

D1 (max device diameter with diamonds)=530 μm

D2 (device diameter without active diamonds layer)=500 μm

L (Channel average length)=2000 μm d (Channel diameter after expected recoil)=?

A (Removed cross section area)=$\pi/4*(D1^2-D2^2)$ =24268 $\mu m^2$ $A=\pi*d^2/4 \Rightarrow d\sim 160$ μm V (Volume)=L*A=48,536,000 $\mu m^3$ W (Weight)=V*density=48.5 μgr.

As can be seen, the two results are very close which provides a good estimation of the method's efficacy.

The above embodiments, examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

The invention claimed is:

1. A device for creating a channel having predetermined dimensions in an eye wall, the device comprising an elongated member extending along a longitudinal axis X between a first end and a second end;
   said first end comprising an engagement element configured for engagement with a grip unit comprising a rotor to cause rotation of said elongated member about said longitudinal axis X upon actuation of the rotor to create said channel;
   said second end comprising a tissue piercing tip configured for piercing the eye wall during insertion of the device along said longitudinal axis X into the eye wall;
   said elongated member comprising a segment proximal to the second end extending along said longitudinal axis X and configured for creating said channel by said rotation, said segment having an external surface having a circumference C and comprising:
      at least one depression axially extending along at least a portion of said segment; and
      one or more blades with a cutting edge, extending peripherally beyond said circumference C of said external surface, by a distance defining a cutting thickness, the one or more blades extending along at least part of said segment;
   said device comprising a protective member configured and operable to:
      be fixedly attached to the grip unit at a proximal end of the protective member,
      have a lumen surrounding the elongated member and in which the elongated member is entered from its first end to be engaged by the engagement element with the grip unit,
      have a predetermined length defining a length of the elongated member that penetrates the eye,
      have a shape configured to penetrate through conjunctiva tissue of the eye wall and to form a stopper to prevent excessive penetration of the elongated member into sclera tissue of the eye wall and to block the device from penetrating the eye to an extent that causes damage to inside of the eye, and
      be static during rotation of the elongated member thereby protecting the surrounding conjunctiva tissue during the channel creation in the eye wall.

2. The device of claim 1, wherein said depression is sealed proximal to said second end.

3. The device of claim 1, wherein said second end is beveled towards the tissue piercing tip, the tip being collinear with said axis X.

4. The device of claim 1, wherein said one or more blades comprise a cutting edge radially distanced from said circumference C by about 2-100 μm.

5. The device of claim 1, wherein during rotation about said axis X, said one or more blades are configured to cut a layer of tissue around said external surface, said layer having a thickness equal or less than the cutting thickness.

6. The device of claim 1, comprising a ridge along said external surface radially extending opposite to at least one blade.

7. The device of claim 1, having one of the following configurations: comprising a single blade and a single depression, both extending along at least part of said segment; and comprising or more than one blade and respectively more than one depression, each depression juxtaposed to a blade.

8. The device of claim 1, wherein the depression comprises one or more partition walls dividing the depression into, respectively, two or more compartments, said one or more partition walls providing full or partial separation between the respectively two or more compartments.

9. The device of claim 1, having a nominal diameter of between 100-1,000 µm.

10. The device of claim 1, wherein said elongated member further comprising a gap section having a length defined between said second end and said depression of between 100-2500 µm.

11. The device of claim 1, wherein said piercing end has a tip angle of between 5° and 15°.

12. The device of claim 1, wherein said depression comprises an inner surface and at least one barrier extending inwardly from said inner surface.

13. The device of claim 1, wherein said depression has a length along said axis X of between 100-2,500 µm.

14. A device for creating a channel having predetermined dimensions in an eye wall, the device comprising an elongated member extending along a longitudinal axis X between a first end and a second end,
said first end comprising an engagement element configured for engagement with a grip unit comprising a rotor to cause rotation of said device about said longitudinal axis X upon actuation of the rotor to create said channel,
said second end comprising a tissue piercing tip configured for piercing the eye wall during insertion of the device along said longitudinal axis X into the eye wall;
said elongated member comprising a segment proximal to the second end extending along said longitudinal axis X and configured for creating said channel by said rotation, said segment having an external surface having a circumference C and comprising a roughened file-like external surface having a plurality of protrusions protruding outwardly from said circumference C and extending outwardly beyond the circumference C, and a plurality of valleys, multiple ones of the plurality of valleys being positioned between multiple ones of the plurality of protrusions in both longitudinal and circumferential directions, and the roughened file-like external surface extending along a part of said segment in the longitudinal direction and around all of said segment in the circumferential direction;
said protrusions and valleys determining amount of tissue scrapped off from the eye wall during said rotation of the device, thereby defining said predetermined dimensions of the channel;
the device comprising a protective member configured and operable to:
be fixedly attached to the grip unit at a proximal end of the protective member,
have a lumen surrounding the elongated member and in which the elongated member is entered from its first end to be engaged by the engagement element with the grip unit,
have a predetermined length defining a length of the elongated member that penetrates the eye,
have a shape configured to penetrate through conjunctiva tissue of the eye wall and to form a stopper to prevent excessive penetration of the elongated member into sclera tissue of the eye wall and to block the device from penetrating the eye to an extent that causes damage to inside of the eye, and
be static during rotation of the elongated member thereby protecting the surrounding conjunctiva tissue during the channel creation in the eye wall.

15. A device for creating a channel having predetermined dimensions in an eye wall, the device comprising an elongated member extending along a longitudinal axis X between a first end and a second end,
said first end comprising an engagement element configured for engagement with a grip unit comprising a rotor to cause rotation of said device about said longitudinal axis X upon actuation of the rotor to create said channel,
said second end comprising a tissue piercing tip configured for piercing the eye wall during insertion of the device along said longitudinal axis X into the eye wall;
said elongated member comprising a segment proximal to the second end extending along said longitudinal axis X, said segment having an external surface having a circumference C and comprising:
at least one depression extending both circumferentially across and longitudinally along at least a portion of said segment; and
a plurality of blades extending along at least part of said segment with cutting edges extending up to and not exceeding said circumference C; and
a protective member configured and operable to:
be fixedly attached to the grip unit at a proximal end of the protective member,
have a lumen surrounding the elongated member and in which the elongated member is entered from its first end to be engaged by the engagement element with the grip unit,
have a predetermined length defining a length of the elongated member that penetrates the eye,
have a shape configured to penetrate through conjunctiva tissue of the eye wall and to form a stopper to prevent excessive penetration of the elongated member into sclera tissue of the eye wall and to block the device from penetrating the eye to an extent that causes damage to inside of the eye, and
be static during rotation of the elongated member thereby protecting the surrounding conjunctiva tissue during the channel creation in the eye wall.

16. The device of claim 15 further comprising one or more partition walls extending transversely at respective locations along said depression in a manner so as to thereby divide said depression into two or more successive compartments along the segment and prevent flow of fluid through said depression from one side to another side of the device.

17. A method for creating a channel in an eye wall, the method comprising the steps of:
providing a medical assembly comprising a grip unit and a device as claimed in claim 1, mounted thereon;
piercing the eye wall with the tissue piercing tip of the device and sliding the device along a longitudinal axis X into the eye wall to a desired depth within the eye wall, the predetermined length of the protective member defining a length of the elongated member that penetrates the eye;

penetrating the protective member through conjunctiva tissue of the eye wall, while the protective member forms a stopper to prevent excessive penetration of the elongated member into sclera tissue of the eye wall and to block the device from penetrating the eye to an extent that causes damage to inside of the eye;

actuating said medical assembly while the device is embedded in the eye wall to allow at least one full rotation about said axis X, during said rotation soft tissue of the eye wall is scrapped around the external surface of said segment;

maintaining the protective member static during rotation of the elongated member thereby protecting the surrounding conjunctiva tissue during the channel creation in the eye wall; and upon termination of rotations, removing the device from the eye wall, leaving a channel within said tissue wall.

18. A method for reducing intraocular pressure in an eye, the method comprising:

providing a medical assembly comprising a grip unit and a device as claimed in claim 1, mounted thereon; and creating, through use of the device by piercing the conjunctiva with the second end and forwarding the device into the sclera and piercing the sclera with the second end and rotating the device around the longitudinal axis X, a drainage channel in the sclero-corneal junction area of the eye;

the predetermined length of the protective member defining a length of the elongated member that penetrates the eye, the creating of the drainage channel comprising penetrating the protective member through conjunctiva tissue of the eye wall, while the protective member forms a stopper to prevent excessive penetration of the elongated member into sclera tissue of the eye wall and to block the device from penetrating the eye to an extent that causes damage to inside of the eye;

the rotating of the device comprising maintaining the protective member static during rotation of the elongated member thereby protecting the surrounding conjunctiva tissue during the channel creation in the eye wall;

the drainage channel extending from the interface between the sclera and the conjunctiva to the anterior chamber of the eye, the drainage channel having a diameter of no more than 200 µm after recoil of the tissue.

19. A method for reducing intraocular pressure in an eye, the method comprising:

providing a medical assembly comprising a grip unit and a device as claimed in claim 14, mounted thereon; and creating, through use of the device by piercing the conjunctiva with the second end and forwarding the device into the sclera and piercing the sclera with the second end and rotating the device around the longitudinal axis X, a drainage channel in the sclero-corneal junction area of the eye;

the predetermined length of the protective member defining a length of the elongated member that penetrates the eye, the creating of the drainage channel comprising penetrating the protective member through conjunctiva tissue of the eye wall, while the protective member forms a stopper to prevent excessive penetration of the elongated member into sclera tissue of the eye wall and to block the device from penetrating the eye to an extent that causes damage to inside of the eye;

the rotating of the device comprising maintaining the protective member static during rotation of the elongated member thereby protecting the surrounding conjunctiva tissue during the channel creation in the eye wall;

the drainage channel extending from the interface between the sclera and the conjunctiva to the anterior chamber of the eye, the drainage channel having a diameter of no more than 200 µm after recoil of the tissue.

20. A method for creating a channel in an eye wall, the method comprising the steps of:

providing a medical assembly comprising a grip unit and a device as claimed in claim 14, mounted thereon;

piercing the eye wall with the tissue piercing tip of the device and sliding the device along a longitudinal axis X into the eye wall to a desired depth within the eye wall, the predetermined length of the protective member defining a length of the elongated member that penetrates the eye;

penetrating the protective member through conjunctiva tissue of the eye wall, while the protective member forms a stopper to prevent excessive penetration of the elongated member into sclera tissue of the eye wall and to block the device from penetrating the eye to an extent that causes damage to inside of the eye;

actuating said medical assembly while the device is embedded in the eye wall to allow at least one full rotation about said axis X, during said rotation soft tissue of the eye wall is scrapped around the external surface of said segment;

maintaining the protective member static during rotation of the elongated member thereby protecting the surrounding conjunctiva tissue during the channel creation in the eye wall; and upon termination of rotations, removing the device from the eye wall, leaving a channel within said tissue wall.

21. A method for reducing intraocular pressure in an eye, the method comprising:

providing a medical assembly comprising a grip unit and a device as claimed in claim 15, mounted thereon; and creating, through use of the device by piercing the conjunctiva with the second end and forwarding the device into the sclera and piercing the sclera with the second end and rotating the device around the longitudinal axis X, a drainage channel in the sclero-corneal junction area of the eye;

the predetermined length of the protective member defining a length of the elongated member that penetrates the eye, the creating of the drainage channel comprising penetrating the protective member through conjunctiva tissue of the eye wall, while the protective member forms a stopper to prevent excessive penetration of the elongated member into sclera tissue of the eye wall and to block the device from penetrating the eye to an extent that causes damage to inside of the eye;

the rotating of the device comprising maintaining the protective member static during rotation of the elongated member thereby protecting the surrounding conjunctiva tissue during the channel creation in the eye wall;

the drainage channel extending from the interface between the sclera and the conjunctiva to the anterior chamber of the eye, the drainage channel having a diameter of no more than 200 μm after recoil of the tissue.

\* \* \* \* \*